(12) United States Patent
Milner et al.

(10) Patent No.: US 11,779,220 B2
(45) Date of Patent: Oct. 10, 2023

(54) MULTI-CHANNEL ORTHOGONAL CONVOLUTIONAL NEURAL NETWORKS

(71) Applicant: Research Development Foundation, Carson City, NV (US)

(72) Inventors: Thomas E. Milner, Austin, TX (US); Austin McElroy, Austin, TX (US); Aydin Zahedivash, Austin, TX (US); Nitesh Katta, Austin, TX (US)

(73) Assignee: Research Development Foundation, Carson City, NV (US)

( * ) Notice: Subject to any disclaimer, the term of this patent is extended or adjusted under 35 U.S.C. 154(b) by 778 days.

(21) Appl. No.: 16/712,122

(22) Filed: Dec. 12, 2019

(65) Prior Publication Data

US 2020/0187790 A1 Jun. 18, 2020

Related U.S. Application Data

(60) Provisional application No. 62/779,888, filed on Dec. 14, 2018.

(51) Int. Cl.
*A61B 5/00* (2006.01)
*A61B 5/02* (2006.01)
(Continued)

(52) U.S. Cl.
CPC ........ *A61B 5/0066* (2013.01); *A61B 5/02007* (2013.01); *A61B 6/4241* (2013.01);
(Continued)

(58) Field of Classification Search
CPC . A61B 5/02007; A61B 5/0066; A61B 6/4241; A61B 2562/0233; A61B 5/0084; A61B 5/6852; A61B 5/7264; G06K 9/6269; G06N 3/0454; G06N 3/08; G06T 7/0012; G06T 11/003; G06T 2207/20081; G06T 2207/20084; G06T 2207/30024; G06T 2207/10068; G06T 2207/10101; G06T 2207/30101; G06V 10/764; G06V 10/82; G06V 2201/03
See application file for complete search history.

(56) References Cited

U.S. PATENT DOCUMENTS 5,995,651 A 11/1999 Gelenbe et al.
7,676,076 B2 3/2010 Spahn
(Continued)

FOREIGN PATENT DOCUMENTS

WO WO 2009/149131 12/2009
WO WO 2017/214421 12/2017

OTHER PUBLICATIONS

Athanasiou et al. "Methodology for fully automated segmentation and plaque characterization in intracoronary optical coherence tomography images," *Journal of Biomedical Optics*, 19(2):26009, 2014.
(Continued)

*Primary Examiner* — Tom Y Lu
(74) *Attorney, Agent, or Firm* — Parker Highlander PLLC

(57) ABSTRACT

Exemplary embodiments of the present disclosure include apparatus and methods to classify the plaque tissue present in the coronary artery using intravascular optical coherence tomography (IVOCT) images.

5 Claims, 9 Drawing Sheets
(3 of 9 Drawing Sheet(s) Filed in Color)

(51) Int. Cl.

| | | |
|---|---|---|
| *G06T 7/00* | (2017.01) | |
| *G06T 11/00* | (2006.01) | |
| *A61B 6/00* | (2006.01) | |
| *G06F 18/2411* | (2023.01) | |
| *G06N 3/045* | (2023.01) | |
| *G06V 10/764* | (2022.01) | |
| *G06V 10/82* | (2022.01) | |

(52) U.S. Cl.
CPC ......... *G06F 18/2411* (2023.01); *G06N 3/045* (2023.01); *G06T 7/0012* (2013.01); *G06T 11/003* (2013.01); *G06V 10/764* (2022.01); *G06V 10/82* (2022.01); *G06T 2207/20081* (2013.01); *G06T 2207/20084* (2013.01); *G06T 2207/30024* (2013.01)

(56) References Cited

U.S. PATENT DOCUMENTS

| | | | |
|---|---|---|---|
| 9,633,277 | B2 | 4/2017 | Feldman et al. |
| 10,542,954 | B2* | 1/2020 | Spencer ............... A61B 6/485 |
| 2003/0028100 | A1 | 2/2003 | Tearney et al. |
| 2003/0220749 | A1 | 11/2003 | Chen et al. |
| 2009/0306520 | A1 | 12/2009 | Schmitt et al. |
| 2011/0077528 | A1* | 3/2011 | Kemp ............... G01N 21/4795 606/7 |
| 2012/0022360 | A1* | 1/2012 | Kemp ............... A61B 5/1459 600/407 |
| 2012/0163693 | A1 | 6/2012 | Suri |
| 2014/0268168 | A1 | 9/2014 | Feldman et al. |
| 2016/0078309 | A1 | 3/2016 | Feldman et al. |
| 2016/0235373 | A1 | 8/2016 | Sharma et al. |

OTHER PUBLICATIONS

Extended European Search Report issued in European Application No. 17811024.3, dated Nov. 29, 2019.

International Search Report and Written Opinion issued in corresponding PCT Application No. PCT/US2017/036587, dated Oct. 3, 2017.

International Preliminary Report on Patentability issued in corresponding PCT Application No. PCT/US2017/036587, dated Dec. 20, 2018.

International Search Report and Written Opinion issued in corresponding PCT Application No. PCT/US2019/065850, dated Apr. 14, 2020.

Huang et al., "Orthogonal Weight Normalization: Solution to Optimization over Multiple Dependent Stiefel Manifolds in Deep Neural Networks," Cornell University Library, Sep. 16, 2017, https://arxiv.org/abs/1709.06079, pp. 4-5, 7.

Lekadir et al., "A Convolutional Neural Network for Automatic Characterization of Plaque Composition in Carotid Ultrasound," J Biomed Health Inform., Jan. 2017, 21(1), https://www.ncbi.nlm.nh.gov/pme/articles/PMC5293622, p. 48-55.

Baruah et al., "Histology-validated neural networks enable accurate plaque tissue and thin-capped fibroatheroma characterization through intravascular optical coherence tomography," *Circulation*, Abstract 19246, 2018.

Extended European Search Report issued in European Application No. 19895039.6, dated Jul. 13, 2022.

Shalev et al., "Automated volumetric intravascular plaque classification using optical coherence tomography (OCT)," *Proceedings of the Thirtieth AAAI Conference on Artificial Intelligence*, 30(2):4047-4052, 2015.

* cited by examiner

MULTI-CHANNEL ORTHOGONAL CONVOLUTIONAL NEURAL NETWORKS

CROSS-REFERENCE TO RELATED APPLICATIONS

This application claims priority to U.S. Provisional Patent Application Ser. No. 62/779,888, filed Dec. 14, 2018, the entire contents of which are incorporated by reference herein.

BACKGROUND INFORMATION

Atherosclerosis and plaque rupture leading to myocardial infarction remain the leading cause of death worldwide [1]. Inflammation and underlying cellular and molecular mechanisms [2-4] contribute to atherogenesis from initiation through progression, plaque rupture and ultimately, thrombosis. The vulnerable plaque, recently defined by Virmani [5] as "thin-cap fibroatheroma", results from inflammation and is characterized as having a thin fibrous cap typically less than 65 µm thick, increased infiltration of macrophages with decreased smooth muscle cells, and an increased lipid core size compared to stable plaques [6-8].

Several cellular and molecular events that lead to rupture of thin-cap fibroatheromas are now understood and being utilized to develop novel imaging approaches. Accumulations of macrophages in thin-cap fibroatheromas over-express matrix metalloproteinases (MMPs) [9-12] which are believed to contribute to vulnerability of thin-cap fibroatheromas and increased thrombogenicity [13-15]. Macrophages are an important early cellular marker that indicates the risk of plaque rupture in the coronary, cerebral, and peripheral circulations. Since plaque vulnerability is related to cellular composition as well as anatomical structure, developing a diagnostic method that can simultaneously reveal both composition and structure is desirable to identify vulnerable plaques and would allow in vivo monitoring of cardiovascular disease in longitudinal studies in response to cardiovascular interventions.

Intravascular OCT (IVOCT) is a recently developed catheter-based method for high-resolution intravascular imaging. Of the cardiovascular imaging modalities, IVOCT is the only approach that provides sufficient spatial resolution to image thin-cap fibroatheromas.

However, risk of plaque rupture cannot be easily assessed by only IVOCT images. Two-photon luminescence (TPL) microscopy uses nonlinear optical properties of tissue and has been utilized to image plaque components such as endothelial cells, smooth muscle cells [16], elastin fibers [17,18], oxidized LDL [19] and lipid droplets [20] based on their endogenous autofluorescence. More recently, it has been reported that macrophages loaded with nanoparticles can be detected by TPL microscopy [21,22]. Fiber-based OCT [23,24] and TPL microscopy [25-28] has been reported respectively using photonic crystal fibers to transmit broadband light for achieving higher spatial resolution or to transmit ultrashort pulses for system size minimization. However, a combined fiber-based OCT-TPL system has not been previously realized.

Determining arterial plaque composition however can significantly improve early diagnosis of atherosclerosis. Early detection of vulnerable plaque can lead to earlier management of risk factors, improving future clinical outcome, and can give rise to more targeted treatments. Coronary atherosclerotic plaque is generally composed of lipid rich, fibrous, or calcified tissues. Calcified plaques are linked to stable lesions, while lesions with high amounts of fibrous and/or lipid tissue are linked to unstable thin-capped fibroatheroma (TCFA) lesions. TCFAs are particularly risky, being responsible for the majority of acute coronary events, such as plaque ruptures (Fujii et al, 2015). Plaque tissue characterization can also help guide stent placement. Metallic stents placed adjacent to lipid plaques, for example, have displayed non-optimal healing responses while those adjacent to calcified plaques have a higher chance of stent thrombosis or in-stent restenosis (Ughi et al). Thus plaque composition can be particularly predictive of disease and interventional outcome. Furthermore, quantitative characterization of plaque morphologies can advance the understanding of atherosclerosis mechanisms, uncover new diagnostic criteria, and hasten development and testing of new therapies.

Current standards for clinical plaque classification rely on intravascular ultrasound (IVUS) or computed tomography (CT) scans. The current industry standard for quantitative coronary angiography in terms of plaque characterization, IVUS, has not been able to consistently identify fibrous or lipid unstable plaques (Jang et al). This limitation is linked to IVUS's axial resolution of ~100 µm, which makes detection of unstable plaque problematic as these lesions are often under 100 µm in thickness, such as TCFAs measured at <65 µm.

Intravascular optical coherence tomography (IVOCT) however, typically has a 10 µm axial resolution, allowing for the detection of a larger range of plaque sizes. IVOCT uses broadband interferometry from a catheter-mounted light source to generate images based on the refractive indices and reflectivity of sample material. In the case of the coronary artery, backscattered light from the arterial wall is interfered with light at a controlled path length to generate images at various tissue depths of up to 2 mm, making it ideally suited to radially imaging arteries. Additionally, IVOCT can deliver this micron-level resolution in real-time, making it a great tool for noninvasive catheter-based intravascular imaging, in vivo.

Currently, the majority of IVOCT plaque classification is formed on a ground truth that is built visually, with regions of pixels being classified into fibrous, lipid, and calcified tissue one at a time by human experts trained to read OCT images. However, expert analysis of OCT images is prone to mischaracterization. Experiments conducted by Manfrini et al have shown that "misinterpretation [by experts] occurred in 28 OCT images [overall] (41%); 21 fibrous-cap atheromas (31%), 6 fibrocalcific plaques (9%), and 1 fibrous plaque (1%)" (Manfrini et al). Such misinterpretations and dependence on human experts represent one of the most significant barriers to the medical community when making recommendations for IVOCT over IVUS or CT scans for diagnosis and represents a lack of fidelity in the IVOCT field.

Accordingly, the existing plaque classification techniques include many shortcomings, and improved systems and methods are desired.

SUMMARY

Although convolutional neural networks (CNN) have been applied to IVOCT for automatic classification of tissue [124-126], many issues have been identified which are addressed as described herein. CNN that have been developed are traditionally applied to images captured using planar RGB arrays with either a charged coupled device (CCD) or CMOS imaging sensor. These sensors exhibit excellent spatial and temporal correlation with very high signal to noise ratios and no speckle noise.

Medical images are usually not captured using one of these imaging sensors and are constructed using point or linear array transducers. After signal acquisition, the transduced signal has mathematical operations applied and displayed to the user, in the form of grayscale or false color imaging. Optical coherence tomography (OCT), ultrasound, MRI, x-ray, and CT systems, among others, create images in this manner. Furthermore, OCT and ultrasound are coherent imaging methods and thus suffer from speckle, a type of noise that is dependent on the numerical aperture of the sensing device.

Exemplary embodiments of the present disclosure include an apparatus and methods that apply an orthogonal CNN by considering how the images are transduced and constructed, and design neural networks to best consider this information. Whereas square kernels are ideal for square sensors that are temporally and spatially correlated, they may not be ideal for medical images.

In OCT, an A-Scan (also referred to as a reflectivity profile) is the smallest unit of data and is formed either from a point sensor or one-dimensional (1D) array of sensors. These data can be considered temporally and spatially correlated and should be treated as such by the neural networks. In the case of a CNN, this can be expressed as kernels that exist only in the direction of the a-scan with a width of 1 A-Scan. Data across A-Scans should be treated as separate, as A-Scan spacing is not necessarily uniform, and in the case of a CNN, should be treated with an orthogonal 1D kernel.

Considering medical images as a single grayscale image is naive. Medical imaging modalities contain a rich set of derived data that should be considered by a neural network as well. As used herein, the term derived data is data that is mathematically extracted from the original imaging sensor. For example, OCT data is formed from light that is backscattered from the sample. Certain techniques (e.g. including those by Vermeer and de Boer) have been demonstrated to view the attenuation of an OCT A-Scan and may provide a neural network with valuable information when used in conjunction with traditional backscatter OCT data. Other examples of derived data are two-dimensional (2D) standard deviation and other statistical rank metrics. Non-derived data may also be added, depending on the medical imaging system design. Polarization, though not standard on OCT systems, can be added and included as additional dimensions. This multi-dimensional data extracted from an OCT data set can be shaped similar to that of RGB data, except it is not limited by the color channels of the sensor but the number of useful derived or non-derived data that is captured.

Exemplary embodiments include a method of improving discrimination between superficial lipid and calcium versus fibrous tissue and lipid, calcium tissues, and connective tissue, the method comprising: acquiring an image, wherein the image is constructed signal from a point or linear array transducer; analyzing how the image was constructed and mathematically extracting derived data from the image; and applying an orthogonal convolutional neural network (OCNN) to optimize consideration of the derived data.

In certain embodiments, the image is obtained using an optical coherence tomography (OCT) process. In particular embodiments, the derived data comprises attenuation data of an A-scan performed during the OCT process. In some embodiments, the derived data comprises two-dimensional (2D) standard deviation data. Specific embodiments further comprise applying the OCNN to non-derived data. In certain embodiments, the non-derived data comprises polarization data.

Exemplary embodiments of the present disclosure include an automated algorithmic method to classify the plaque tissue present in the coronary artery that is based on IVOCT images co-registered with histology for validation. The described powerful algorithmic method for a tissue classification system based on histology, the clinical gold standard, as its ground truth can bridge the gap between the potential of IVOCT and clinical acceptance.

Exemplary embodiments of the present disclosure include systems and methods for an automated coronary plaque characterization and risk assessment using intravascular optical coherence tomography and a smart-algorithm. Particular embodiments may incorporate optical coherence tomography systems and methods as disclosed in U.S. Patent Publications 2014/0268168 and 2016/0078309, incorporated by reference herein.

Exemplary embodiments include a system comprising: an imaging device comprising an optical coherence tomography light source, wherein the imaging device is configured to obtain an image of intravascular tissue comprising plaque; and a non-transitory computer readable medium configured to: analyze a pixel of the image with a first neural network configured to classify the plaque as a first tissue type of a plurality of tissue types; analyze the pixel of the image with a second neural network configured to classify the plaque as a second tissue type of the plurality of tissue types; and analyze the pixel of the image with a third neural network configured to classify the plaque as a third tissue type of the plurality of tissue types.

In certain embodiments, histological data from the plurality of tissue types is analyzed to characterize tissue types of pixels selected to train the first, second and third neural networks. In particular embodiments, the first tissue type is lipid plaque, the second tissue type is a calcific plaque, and the third tissue type is a fibrous plaque. In some embodiments, the non-transitory computer readable medium is configured to optimize the first, second and third neural networks by evaluating a plurality of features of the image with nodes of the first, second and third neural networks to calculate sensitivity and specificity of the plurality of features using a receiver operating characteristic (ROC) curve. In specific embodiments, the plurality of features comprise one or more of the following Gray Level Co-Occurrence Matrix (GLCM) features: contrast, energy, correlation, homogeneity, entropy, and maximum probability.

In certain embodiments, the plurality of features comprise one or more of the following two-dimensional image statistics: mean value, variance, skewness, kurtosis, and energy. In particular embodiments, the optical coherence tomography light source is configured as a swept source optical coherence tomography light source. In some embodiments, the optical coherence tomography light source is configured as a broadband optical coherence tomography light source. In specific embodiments, the imaging device further comprises a short-pulsed excitation light source. In certain embodiments, the short-pulsed excitation light source is a two-photon luminescence light source.

In particular embodiments, the imaging device further comprises a photonic crystal fiber configured to simultaneously: enable single-mode propagation of a first wavelength from the optical coherence tomography light source to a sample site; enable single-mode propagation of a second wavelength from the short-pulsed light source to the sample site; transmit an optical coherence tomography signal from the sample site, wherein the optical coherence tomography signal is generated from the first wavelength; and transmit an emission signal from the sample site, wherein the emission signal is induced by the second wavelength from the short-pulsed light source.

Specific embodiments further comprise a first dichroic element, and in some embodiments, the first dichroic element is configured to direct the first and second wavelengths to the sample path. Certain embodiments comprise a second dichroic element, and in particular embodiments, the second dichroic element is configured to direct two photon luminescence toward a photon counting detector. Specific embodiments comprise a balanced detector, and in certain embodiments, the balanced detector is configured to minimize a non-interfering OCT component. Particular embodiments comprise a photon counting detector, and in some embodiments the photon counting detector is a photomultiplier tube or an avalanche photo diode. In certain embodiments, the photon counting detector is configured to detect two-photon luminescence.

Particular embodiments include a method of characterizing coronary plaque, the method comprising: obtaining an image of a sample site using an optical coherence tomography light source emitting light from an optical fiber, wherein the image comprises intravascular tissue comprising plaque; analyzing quantitative data of a pixel of the image with a first neural network configured to classify the plaque as a first tissue type of a plurality of tissue types, wherein the first neural network comprises a first plurality of nodes and reads a first plurality of features; analyzing quantitative data of the pixel of the image with a second neural network configured to classify the plaque as a second tissue type of the plurality of tissue types, wherein the second neural network comprises a second plurality of nodes and reads a second plurality of features; and analyzing quantitative data of the pixel of the image with a third neural network configured to classify the plaque as a third tissue type of the plurality of tissue types, wherein the third neural network comprises a third plurality of nodes and reads a third plurality of features.

In certain embodiments, histological data from the plurality of tissue types is analyzed to characterize tissue types of pixels selected to train the first, second and third neural networks. IN particular embodiments, the first tissue type is lipid plaque, the second tissue type is a calcific plaque, and the third tissue type is a fibrous plaque. In some embodiments, the quantitative data includes classifying features comprising one or more of the following: contrast, energy, correlation, homogeneity, entropy, and maximum probability. In some embodiments, the quantitative data includes classifying features comprising one or more of the following: mean value, variance, skewness, kurtosis, and energy. Specific embodiments include optimizing the first, second and third neural networks by calculating a receiver operating characteristic (ROC) curve which plots a true positive versus a false positive rate for a plurality of classifying features of the image. Some embodiments further comprise calculating an area under each receiver operating characteristic (ROC) curve for each of the plurality of classifying features. Some embodiments have the ability to create features by optimally weighting different portions of the input image. Such embodiments do not rely on pre-formed quantitative values or features.

Certain embodiments further comprise ranking the plurality of classifying features by the area under each receiver operating characteristic (ROC) curve for each of the plurality of classifying features. Particular embodiments further comprise calculating a sensitivity and a specificity of the classifying features for the first, second and third neural networks. In some embodiments, the sensitivity is a proportion of known plaque type data points that are correctly classified by each of the first, second and third neural networks. In specific embodiments, the specificity is a ratio of correct classifications to total classifications for a certain category of plaque tissue types for each of the first, second and third neural networks. In certain embodiments, each of the first, second and third neural networks is optimized by selecting a combination of nodes and classifying features for each of the first, second and third neural networks that result in the highest value of a sum of the specificity and sensitivity.

Particular embodiments include a system comprising: an imaging device comprising an optical coherence tomography light source, wherein the imaging device is configured to obtain an image of intravascular tissue; and a non-transitory computer readable medium configured to analyze a pixel of the image with a first neural network configured to classify the intravascular tissue in the image as a first tissue type of a plurality of tissue types. In certain embodiments, a non-transitory computer readable medium configured to perform certain steps may do so via a computer processor or other hardware configured to read the non-transitory computer readable medium. In some embodiments, histological data from a plurality of tissue types is analyzed to characterize tissue types of pixels selected to train the first neural network. In particular embodiments, the non-transitory computer readable medium is configured to analyze the pixel of the image with a second neural network configured to classify the intravascular tissue in the image as a second tissue type of the plurality of tissue types. In some embodiments, the non-transitory computer readable medium is configured to analyze the pixel of the image with a third neural network configured to classify the intravascular tissue in the image as a third tissue type of the plurality of tissue types.

In certain embodiments, histological data from the plurality of tissue types is analyzed to characterize tissue types of pixels selected to train the first, second and third neural networks. In particular embodiments, the first tissue type is lipid plaque, the second tissue type is a calcific plaque, and the third tissue type is a fibrous plaque. In some embodiments, the non-transitory computer readable medium is configured to optimize the first, second and third neural networks by evaluating a plurality of features of the image with nodes of the first, second and third neural networks to calculate sensitivity and specificity of the plurality of features using a receiver operating characteristic (ROC) curve. In specific embodiments, the plurality of features comprise one or more of the following Gray Level Co-Occurrence Matrix (GLCM) features: contrast, energy, correlation, homogeneity, entropy, and maximum probability. In certain embodiments, the plurality of features comprise one or more of the following two-dimensional image statistics: mean value, variance, skewness, kurtosis, and energy.

In particular embodiments, the optical coherence tomography light source is configured as a swept source optical coherence tomography light source. In some embodiments, the optical coherence tomography light source is configured as a broadband optical coherence tomography light source. In specific embodiments, the imaging device further comprises a short-pulsed excitation light source. In certain embodiments, the short-pulsed excitation light source is a two-photon luminescence light source.

In particular embodiments, the imaging device further comprises a photonic crystal fiber configured to simultaneously: enable single-mode propagation of a first wavelength from the optical coherence tomography light source to a sample site; enable single-mode propagation of a second wavelength from the short-pulsed light source to the sample site; transmit an optical coherence tomography signal from the sample site, wherein the optical coherence tomography signal is generated from the first wavelength; and transmit an emission signal from the sample site, wherein the emission signal is induced by the second wavelength from the short-pulsed light source. Some embodiments further comprise a first dichroic element, and in specific embodiments the first dichroic element is configured to direct the first and second wavelengths to the sample path.

Certain embodiments further comprise a second dichroic element, and in particular embodiments the second dichroic element is configured to direct two photon luminescence toward a photon counting detector. Some embodiments further comprise a balanced detector, and in specific embodiments the balanced detector is configured to minimize a non-interfering OCT component. Specific embodiments further comprise a photon counting detector. In certain embodiments the photon counting detector is a photomultiplier tube or an avalanche photo diode. In particular embodiments, the photon counting detector is configured to detect two-photon luminescence.

Certain embodiments include a method of characterizing coronary plaque, where the method comprises: obtaining an image of a sample site using an optical coherence tomography light source emitting light from an optical fiber, wherein the image comprises intravascular tissue comprising plaque; analyzing quantitative data of a pixel of the image with a first neural network configured to classify the plaque as a first tissue type of a plurality of tissue types, wherein the first neural network comprises a first plurality of nodes and reads a first plurality of features; analyzing quantitative data of the pixel of the image with a second neural network configured to classify the plaque as a second tissue type of the plurality of tissue types, wherein the second neural network comprises a second plurality of nodes and reads a second plurality of features; and analyzing quantitative data of the pixel of the image with a third neural network configured to classify the plaque as a third tissue type of the plurality of tissue types, wherein the third neural network comprises a third plurality of nodes and reads a third plurality of features.

In particular embodiments, histological data from the plurality of tissue types is analyzed to characterize tissue types of pixels selected to train the first, second and third neural networks. In some embodiments, the first tissue type is lipid plaque, the second tissue type is a calcific plaque, and the third tissue type is a fibrous plaque. In specific embodiments, the quantitative data includes classifying features comprising one or more of the following: contrast, energy, correlation, homogeneity, entropy, and maximum probability. In certain embodiments, the plurality of features comprise one or more of the following two-dimensional image statistics: mean value, variance, skewness, kurtosis, and energy. Particular embodiments further comprise optimizing the first, second and third neural networks by calculating a receiver operating characteristic (ROC) curve which plots a true positive versus a false positive rate for a plurality of classifying features of the image.

Some embodiments further comprise calculating an area under each receiver operating characteristic (ROC) curve for each of the plurality of classifying features. Specific embodiments further comprise ranking the plurality of classifying features by the area under each receiver operating characteristic (ROC) curve for each of the plurality of classifying features. Certain embodiments further comprise calculating a sensitivity and a specificity of the classifying features for the first, second and third neural networks. In particular embodiments, the sensitivity is a proportion of known plaque type data points that are correctly classified by each of the first, second and third neural networks. In some embodiments, the specificity is a ratio of correct classifications to total classifications for a certain category of plaque tissue types for each of the first, second and third neural networks. In specific embodiments, each of the first, second and third neural networks is optimized by selecting a combination of nodes and classifying features for each of the first, second and third neural networks that result in the highest value of a sum of the specificity and sensitivity.

Certain embodiments include a system comprising: an imaging device comprising an optical coherence tomography light source, wherein the imaging device is configured to obtain an image of intravascular tissue; and a non-transitory computer readable medium configured to analyze a pixel of the image with a first neural network configured to classify the intravascular tissue in the image as a first tissue type of a plurality of tissue types. In particular embodiments, histological data from a plurality of tissue types is analyzed to characterize tissue types of pixels selected to train the first neural network. In some embodiments, the non-transitory computer readable medium is configured to analyze the pixel of the image with a second neural network configured to classify the intravascular tissue in the image as a second tissue type of the plurality of tissue types. In specific embodiments, the non-transitory computer readable medium is configured to analyze the pixel of the image with a third neural network configured to classify the intravascular tissue in the image as a third tissue type of the plurality of tissue types.

In some embodiments, to further improve discrimination between the three classified tissue types, fibrous, calcium and lipid, individual A-scans in IVOCT images undergo preprocessing and classification. First individual A-scans are delimited to signal from the start of the lumen boundary to where the signal is attenuated. Additionally, the region of steepest signal decay is also isolated from each A-scan. In an exemplary embodiment, this can be accomplished by using panning windows which apply an algorithm approximating rate of change in signal intensity. Rapid exemplary embodiments can have an algorithm where slope is calculated between intensity values at the end points of a window. Other embodiments may apply first or second derivative algorithms Window sizes must be optimized to measure change in slope with precision without being too computationally expensive. Analysis of A-scans is conducted by extracting statistical signal features and features derived from a gaussian fit. Statistical features in an exemplary embodiment would include area under the entire A-scan signal and corresponding region of interest, and the starting and ending points of the region of steepest signal decay. For gaussian analysis, entire A-scans and the isolated region of steepest signal decay are mirrored to create a symmetric signal distribution. This mirrored distribution is fitted to a gaussian function of the following equation:

$$f(x) = ae^{-\frac{(x-b)^2}{2c^2}}$$

Variables a, b, and c from the equation above are collected as features for each mirrored distribution. Additionally, Goodness of Fit (GOF) to the gaussian is calculated as a feature for each mirrored signal. The statistical and gaussian features can be fed into a classifier, like Linear Discriminant Analysis in an exemplary embodiment, to classify each A-scan as corresponding to Lipid, Fibrous, or Calcium tissue. This classification is then used to threshold the outputs of a neural network.

Neural network outputs have a threshold applied to them to generate a classification into a certain tissue type. After pixels from B-scans are fed into the neural networks and outputs generated, the A-scans these pixels exist within are determined and registered. Neural network outputs then have a threshold applied to them to bias classification towards the classification determined in A-scan processing. For example, If an A-scan was classified as Lipid in the preprocessing stage, then the very hard to meet or high thresholds would be applied to Calcium and Fibrous neural network outputs, while the Lipid network outputs would only have to exceed a threshold of 0.5. This would make classification into a category other than Lipid for any pixels in this A-scan only possible in high unambiguous cases.

Certain embodiments include a method of improving discrimination between superficial lipid and calcium versus fibrous tissue and lipid, calcium tissues, and connective tissue, the method comprising: (1) creating a database of a-scans characteristic of each fibrous, calcium, lipid, and connective tissue based on histology and user input; (2) parsing individual a-scans one at a time from a b-scans; (3) delimiting a tissue region; (4) identifying an index of an initiation of a signal decay region; (5) identifying an index of a termination of the signal decay region; (6) calculating a goodness-of-fit (GOF) to a Gaussian function; (7) extracting a denominator coefficient in the Gaussian function; (8) calculating an area under a signal decay region; (9) calculating an area under a total delimited tissue region; and (10) inputting statistics from steps (4) and (5) into a linear discrimination analysis (LDA) trained on the database to classify an a-scan as fibrous, calcium or lipid.

Particular embodiments further comprise biasing thresholds on a neural network based on a-scan classification obtained in step (10) above. In some embodiments, delimiting a tissue region comprises sampling from a start of a lumen to a point where an intensity is five percent of a maximum intensity. In specific embodiments, identifying an index of an initiation of a signal decay region comprises: using a panning window algorithm where slope is calculated between intensity values at end points of a window; and determining a signal decay region iwhen five consecutive windows show a negative slope. In certain embodiments, identifying an index of a termination of the signal decay region comprises identifying five consecutive windows with positive slope one in the signal decay region.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

DETAILED DESCRIPTION OF ILLUSTRATIVE EMBODIMENTS

Figure 1:
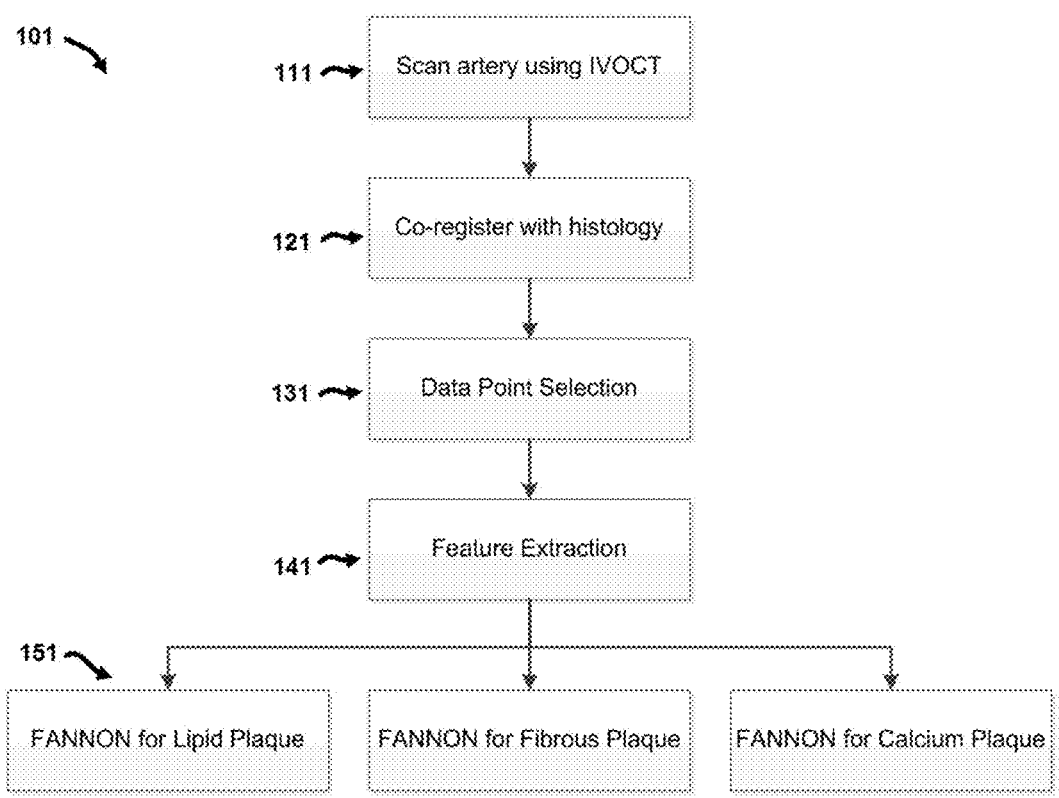
FIG. 1 shows a schematic of a method according to an exemplary embodiment.
Figure 2:
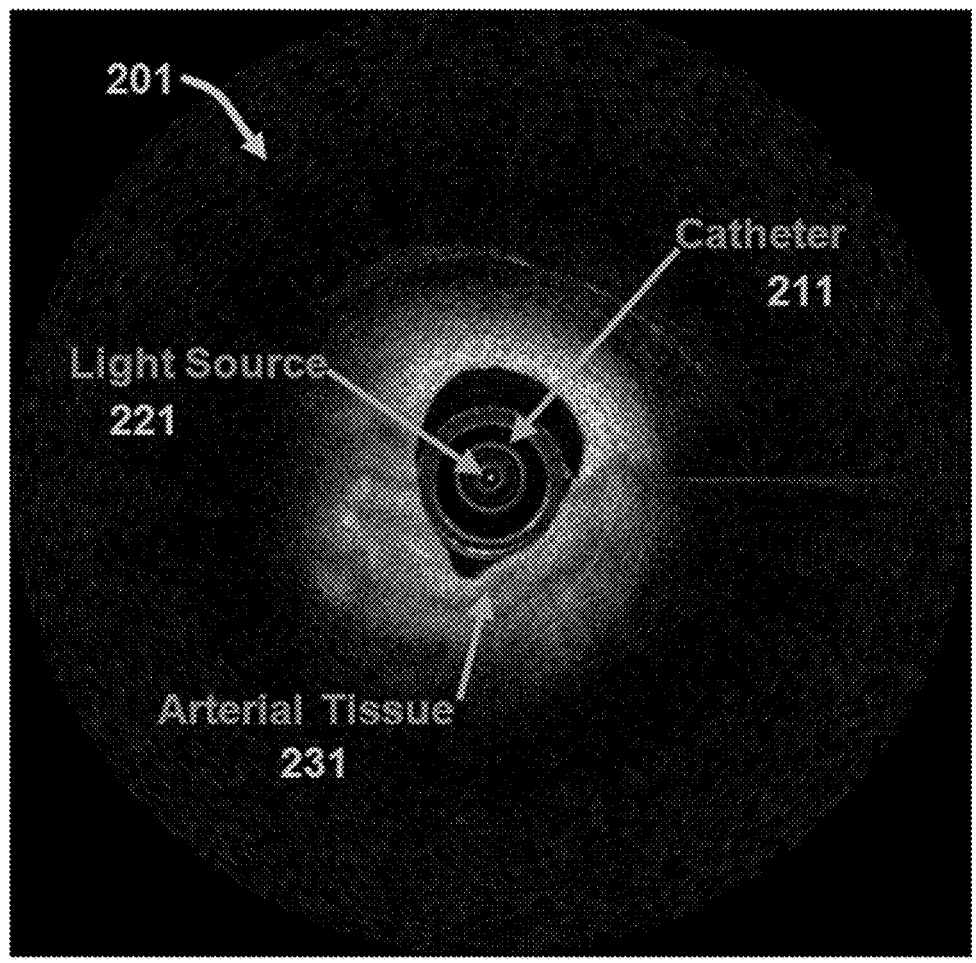
FIG. 2 shows an image obtained from an IV-OCT system.

Referring now to FIG. 1, an overview of an exemplary method 101 comprises various steps performed to classify different types of tissue observed in intravascular optical coherence tomography images. An outline of exemplary methods and systems will be presented initially, followed by more detailed discussion of specific features and elements. As shown in the exemplary embodiment of FIG. 1, method 101 comprises a first step 111 of scanning an artery to obtain intravascular optical coherence tomography images. An example of one such image 201 is provided in FIG. 2. In image 201, a catheter 211 with a light source 221 is used to image arterial tissue 231. It is understood that not all components of catheter 211 are labeled in FIG. 2 for purposes of clarity. As previously noted, in particular embodiments such images may be obtained using optical coherence tomography systems and methods as disclosed in U.S. Patent Publications 2014/0268168 and 2016/0078309, incorporated by reference herein.

In the embodiment disclosed in FIG. 1, method 101 then co-registers image data with histological data in step 121, as described in more detail below. Image data point selection is performed in step 131, followed by feature extraction in step 141, also further discussed below. Feature and Node Optimized Neural Networks (FANONN) for different types of tissue (e.g. lipid plaque, fibrous plaques, and calcific plaques) can then be used to classify the tissue in the image in step 151. In exemplary embodiments, image data point selection may be manually selected by a user (e.g. "point-and-click" selection), or via sampling from regions of interest in B-scans of the tissue. It is understood that the classification techniques disclosed herein may be applied to other tissue types (including non-diseased tissues) as well.

Figure 3:
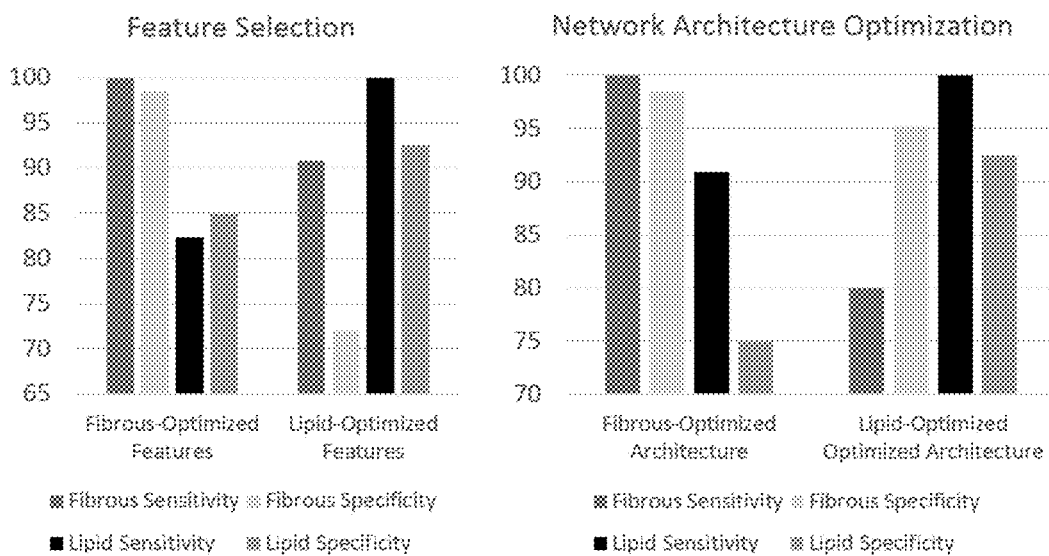
FIG. 3 shows graphs for feature selection and network architecture optimization.

Referring now to FIG. 3 graphs are provided for feature selection and network architecture optimization for fibrous-optimized and lipid-optimized features and architecture. As shown in the graph on the left side of FIG. 3, sensitivity and specificity is highest for a neural network with features selected to optimize for classification of a specific tissue. Lipid sensitivity and specificity is worse with a network running on features optimized for fibrous plaque. Likewise, fibrous sensitivity and specificity is worse with a network running on features optimized for lipid plaque.

The graph on the right side of FIG. 3 illustrates that sensitivity and specificity is highest for a neural network with number of nodes (e.g. neurons) optimized for classification of a specific tissue type. Lipid sensitivity and specificity is worse with a network with number of nodes optimized for fibrous plaque. Likewise, fibrous tissue sensitivity and specificity is worse with a network with number of nodes optimized for lipid tissue. Accordingly, tissue classification is dependent on both the specific features used and the number of nodes comprising the network.

As previously mentioned, exemplary embodiments co-register intravascular OCT image data with histological data. In one example, IVOCT imaging was conducted on 10 human hearts (from 3 women and 7 men) collected within 24 hours of death. The age at death was 65±11 years. Imaging was conducted on 14 coronary arteries (n=10, left anterior descending artery [LAD]; n=4 right coronary artery [RCA]). From these artery scans, image data points were extracted.

IVOCT imaging was conducted using a 1310 nm swept source laser (HSL-1000, Santec, Hackensack, N.J.) with a bandwidth of 80 nm scanning, a repetition rate of 34 kHz, and a measured free-space axial resolution of 20 µm with a 2.8 mm scan depth. The IVOCT signal was sampled with a linear k-space clock to allow real-time OCT image acquisition and display. Per artery, 100 cross-section images (B-scans) were collected. A fluoroscopy system (GE Medical Systems) and a chamber designed to maintain the tissue at 37° C. were used. Left and right coronary 6F guide catheters were sewn into the coronary ostia, 0.014 inch guide-wire access to the coronary arteries was gained under fluoroscopic guidance, and a stent was deployed 80 mm from the guide catheter tip as a fiduciary marker. IVOCT pullbacks were acquired from the stent to the guide catheter (80 mm total pullback length). The left anterior descending (LAD) artery and right coronary artery (RCA) were imaged. Following imaging, the RCA and LAD were perfusion-fixed with formalin at 100 mm Hg. Histology cross-sections were taken from the same 14 coronary arteries and 10 human hearts with 100 histology slices at the same depth as 100 cross-section B-scans for each artery.

To conduct histology after IVOCT imaging, LADs and RCAs were perfusion-fixed with 10% neutral-buffered formalin, excised from each heart, individually radiographed on a Faxitron MX-20 (Faxitron Bioptics LLC, Tucson Ariz.), and decalcified overnight with Cal-Rite (Richard Allen Scientific) if necessary. The arterial segments were sliced into 2-3 mm thick rings and further processed on a Tissue-Tek Vacuum Infiltration Processor (Sakura Finetek USA, Torrance, Calif.) for standard paraffin-embedded sections. An average of 25 rings were generated from each artery. Serial tissue sections (5 µm thick) were cut at 150-µm intervals and stained with hematoxylin and eosin (H&E), modified Movat's pentachrome, and Von Kossa. Anti-CD68 (Dako North America, Inc, Carpinteria, Calif.) and anti-a-smooth muscle cell-actin (Sigma-Aldrich, St. Louis, Mo.) antibodies were used in immunohistochemical studies to identify macrophages and smooth muscle cells, respectively.

In this embodiment, histology rings were then matched to respective IVOCT frames. Co-registration was performed between IVOCT images and histological sections based on the following: (1) two fiducial landmarks—a stent deployed at the distal end of the pullback and the sewn-in guide catheter at the proximal edge—that were visible in IVOCT images, fluoroscopy, and radiography before histopathological processing, and (2) the physical position of IVOCT images in the pullbacks measured against the estimated distance in microns from the fiducial landmarks in the tissue sections.

Classification was automated based on a series of quantifiable image features acquired using an IVOCT scan of the coronary artery. Extraction of image data for classification of plaque required reading specific quantitative measures from the images, known as quantitative features. The quantitative feature set was created using two-dimensional windowed image statistics along with Gray Level Co-Occurrence Matrix (GLCM) textural features and are explained herein.

In this embodiment, the two-dimensional windowed image statistics are determined by generating a square window around a pixel of interest and calculating the following statistics:
(1) Mean Value
(2) Variance
(3) Skewness
(4) Kurtosis
(5) Energy These measures are calculated for both the horizontal and vertical averages within the square window with both image intensity and attenuation data. The intensity is defined as the backscattered light from the tissue measured in decibels. The attenuation data represents how the backscattered light intensity decays as a function of radial distance from the light source.

The GLCM is a method for texture analysis and characterization based on the spatial relationship between pixels.

In this method, image texture is characterized by determining the frequency with which pairs of pixels with certain values and a pre-defined spatial relationship occur. In exemplary embodiments, specific GLCM textural features include:

(1) Contrast
(2) Energy
(3) Correlation
(4) Homogeneity
(5) Entropy
(6) Max Probability Each of these textural features is again calculated with intensity and attenuation. The optimization process for the algorithm to classify each tissue type selects from these windowed and GLCM features. Additional discussion of GLCM can be found in Yang, Xiaofeng, et al. "Ultrasound GLCM texture analysis of radiation-induced parotid-gland injury in head-and-neck cancer radiotherapy: an in vivo study of late toxicity." Medical physics 39.9 (2012): 5732-5739, incorporated by reference herein.

In exemplary embodiments, a classification technique uses an optimized neural network to classify plaque tissue from a set of images. A neural network has the ability to sort a dataset into many different classes. In the embodiment disclosed herein, three different classes of tissue types are identified: lipid, calcium, and fibrous plaque. It is understood that different embodiments may include different classes of tissue types.

A set of quantitative image features is provided to the network as a basis for judgment and using these features, the neural network will make decisions as to what class to sort a pixel into.

There are several design considerations associated with the use of these quantitative features, however. First, the sensitivity and specificity of a neural network can change based on the features that are provided to it. All of the available features to be inputted into the neural network are called candidate features. For example, if one has 300 candidate features to choose from, it might be found that the neural network functions best with a specific set of 150 of those features instead of the full 300. In order to best classify data, the best features should be selected amongst a pool of candidates. Having either too few or too many features than optimum can be damaging to the resulting sensitivity and specificity of the method.

IVOCT expert imaging technicians typically use different features to classify different types of plaque. For example, when looking for fibrous plaque, imaging technicians will typically look for high backscattering and homogeneity whereas when searching for calcium plaque an expert might look at signal quality and delineation of tissue borders. Accordingly, it is not optimal to use a single network with a single set of features to classify all types of tissue.

As previously mentioned in the discussion of FIG. 3, a set of features that work best for sorting fibrous plaque will not be the best features to use for sorting calcific plaque. Furthermore, the number of nodes comprising the neural network affects its performance with a given set of features. The optimal set of features and network structure are interdependent because the inputted features affect the optimal distribution of weights associated with the connections between nodes in the network and this can have an impact on sensitivity and specificity. Therefore, in order to construct an optimized network, one must optimize not only the features selected to classify the tissue but also the structure of a network based on the features used.

Accordingly, exemplary embodiments of the present disclosure utilize a multiple-pass, co-optimized classification system for each tissue type. The method maximizes the sensitivity and specificity for each type of tissue. The classification system first gathers the quantitative image features associated with the IVOCT image data along with the truth data from co-registered histology slides of the tissue. Each type of tissue is handled individually. In the embodiment disclosed herein, a first network is optimized to detect fibrous plaque, then another network is optimized to detect calcific plaque, and a third network is optimized to detect lipid plaque. It is understood, that for additional tissue classes, additional networks can be constructed.

Figure 4:
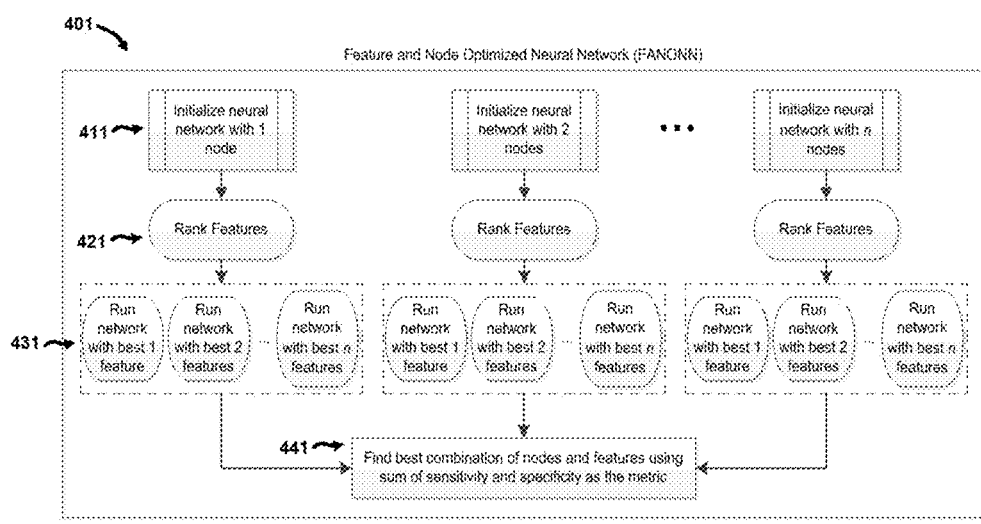
FIG. 4 shows a schematic of a feature and node optimized neural network (FANNON) optimization process.

Referring now to FIG. 4, the feature and node optimized neural network (FANNON) optimization process 401 for each tissue begins by using each feature individually to evaluate the data with a neural network to sort each tissue type. The process begins by initializing a neural network with one node in step 411. The resulting sensitivity and specificity of each feature method is calculated using a receiver operating characteristic (ROC) curve which plots the true positive vs. false positive rates of the classifier. The greater the area under the ROC curve, the greater the sensitivity and specificity of the neural network based on the feature. In step 421, the features are all ranked according to the area under the ROC curves of the neural networks they serve as inputs to, from greatest sensitivity and specificity to least sensitivity and specificity.

After the rank features step in 421, the classification system uses an increasing number of features from the ranked feature list, starting from 1 to the number of candidate features, and records the sensitivity and specificity of each group of features in step 431. This process is repeated for a range of neural network architectures, varying the number of nodes involved. In step 441, the best combination of number of features and nodes used is selected based on the sum of sensitivity and specificity of the network to detect the specific type of tissue involved. The best network for each tissue type has a unique feature set and a unique number of nodes paired together, creating a Feature and Node Optimized Neural Network (FANONN) that is used to optimally classify each plaque type.

Results

The FANONN classification algorithm of exemplary embodiments has been demonstrated to sort plaque tissue as fibrous, calcium, or lipid plaque as verified by histology analysis with sensitivities and specificities listed in the table below:

| | Tissue Type | | |
|---|---|---|---|
| | Ughi et at Accuracy | Athanisiou, Prati, et at ROI overlap Accuracy | FANONN = 10 Testing Set Accuracy |
| Fibrous | 89.5 | 81 | 96.2 |
| Calcium | 72 | 87 | 89.7 |
| Lipid | 79.5 | 71 | 94 |

The data presented in the table above compares results using FANNON techniques disclosed herein to studies in literature that attempt to automate the plaque classification process using IVOCT. The accuracy for each technique is the average of sensitivity and specificity, where the sensitivity is the proportion of the known plaque type data points that the algorithm correctly classifies and the specificity is the ratio of correct classifications to total classifications for a certain category of plaque.

Using accuracy as a reported metric, the direct comparison to current literature studies helps show the power and novelty of the techniques disclosed herein. It should also be noted that the typical current approaches [113, 123] to automated plaque classification are limited in that they are not co-registered with histology, making their classification ground truth weaker.

In addition to this primary classification ability, exemplary embodiments can further classify lipid lesions as the particularly high-risk TCFA type of lesion with 100% sensitivity and 100% specificity. Taken with the classification of lipid plaque as the limiting factor, the algorithm can detect TCFA lesions with 94% accuracy.

Discussion and Conclusion

The described classification techniques and systems can characterize arterial plaque tissue in the coronary artery into fibrous, calcium, or lipid plaque without any human input better than other reported methods. Other groups have conducted similar studies to automate the characterization of coronary plaque with similar motivations but have not had the same degree of success. Specific groups in the field include Ughi et al. who have achieved accuracies of 89.5%, 72%, and 79.5%, and Athanasiou et al. who have achieved accuracies of 81%, 87%, and 71% accuracies in automated characterization of fibrous, calcium, and lipid plaque, respectively. The current leading studies by Ughi and Athanasiou use human observers as their ground truth which makes their classification technique inherently less accurate. In contrast, exemplary embodiment disclosed herein use histology as the ground truth for training which improves accuracy and stability.

Exemplary embodiments of the present disclosure achieve high accuracy through not only the use of histology as the reference truth but also through the classification techniques disclosed herein. Exemplary embodiments achieve improved results by treating each individual plaque type individually and allowing the creation of a tailored neural network structure to optimally classify each type. Such techniques provide for improved results for each plaque type and can be expanded to as many tissue types as desired.

The FANONN classification method disclosed herein not only classifies plaque tissue composition with high accuracy but can also provide risk analysis of the tissue after classification. Of the classified lipid plaque points in an artery, the classification method can identify plaque lesions as TCFA which are known to be indicative of unstable plaque and lead to a majority of acute coronary event such as plaque ruptures (Fujii et al, 2015). Such plaque ruptures can occlude a blood vessel, leading to heart attack or stroke. Unlike previous attempts to classify TCFA lesions via IVUS imaging (Swada), the FANONN smart algorithm paired with the micron-level resolution of IVOCT has both the physical resolution and machine intelligence required to accurately classify these risk-prone plaques. This ability of the classification method makes it very powerful but also special in that no other group in the world can provide automated analysis with a higher degree of accuracy.

Figure 5:
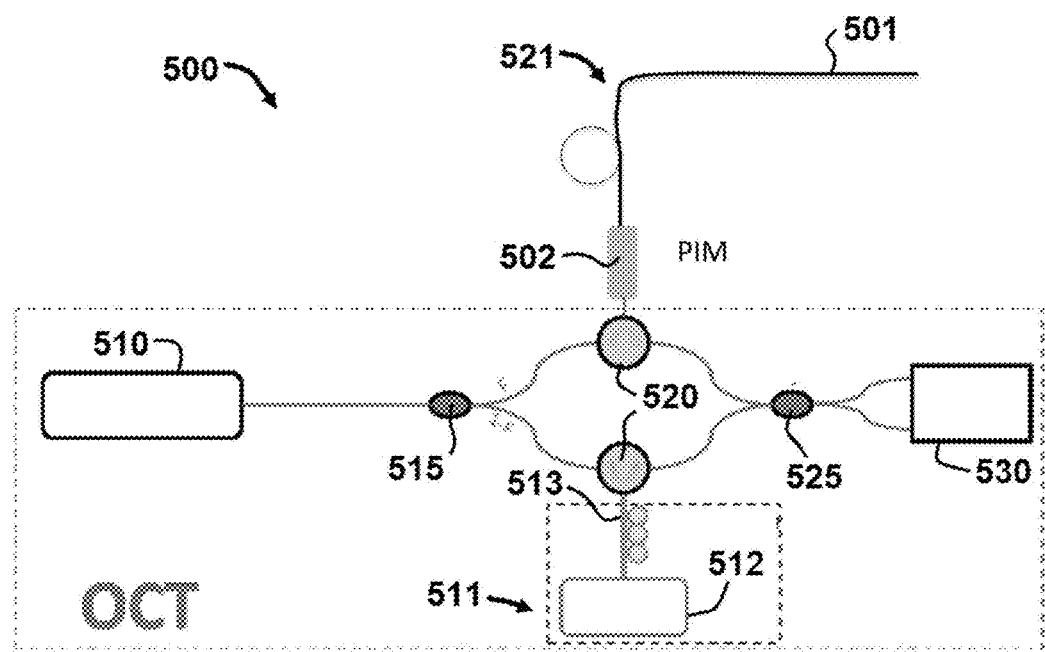
FIG. 5 shows a schematic of an optical coherence tomography system according to exemplary embodiments.

Referring now to FIGS. 5-8, and in particular FIG. 5, an exemplary embodiment of an optical coherence tomography system 500 is shown. System 500 can be used to obtain images of tissue for analysis and classification as described herein. In this embodiment, system 500 comprises an optical coherence tomography light source 510, a splitter 515, optical circulator 520, coupler 525 and balanced detector 530. Splitter 515 is configured to direct light from OCT light source 510 to a reference path 511 and a sample path 521. In the embodiment shown, sample path 521 is directed through patient interface module 502 and catheter 501, while reference path 511 is directed to a fiber reflector 512 via a photonic crystal fiber 513.

Figure 6:
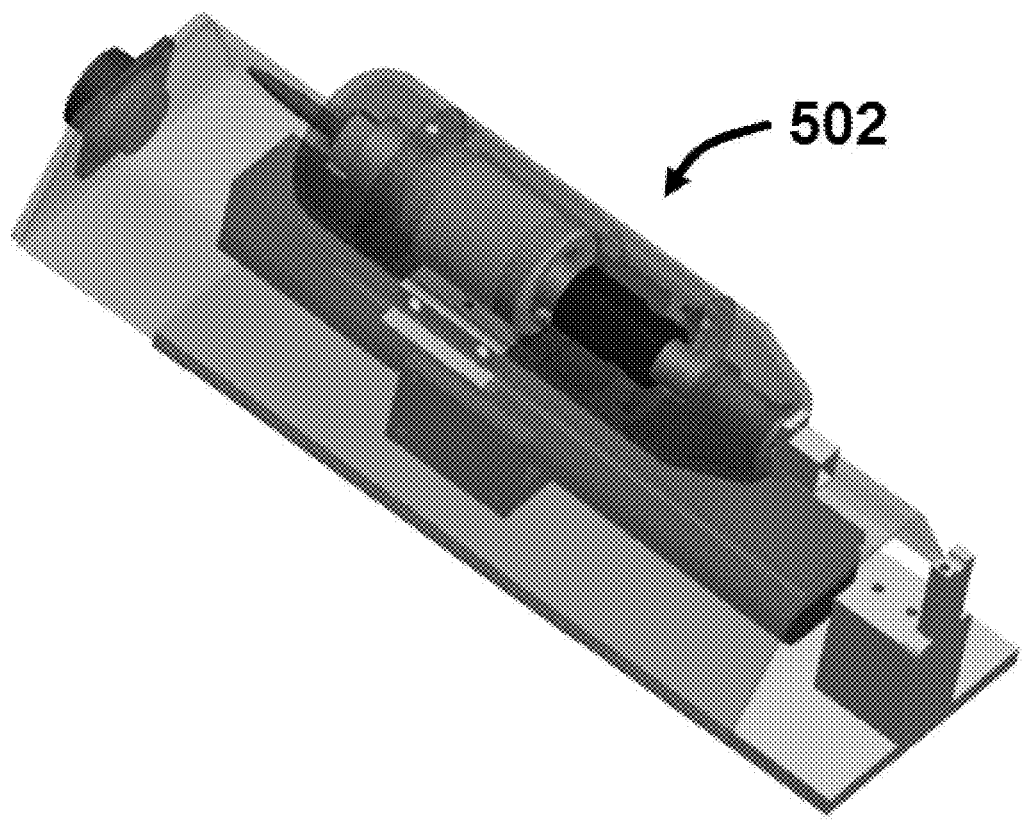
FIG. 6 shows a perspective view of patient interface module of the embodiment of FIG. 5.
Figure 7:
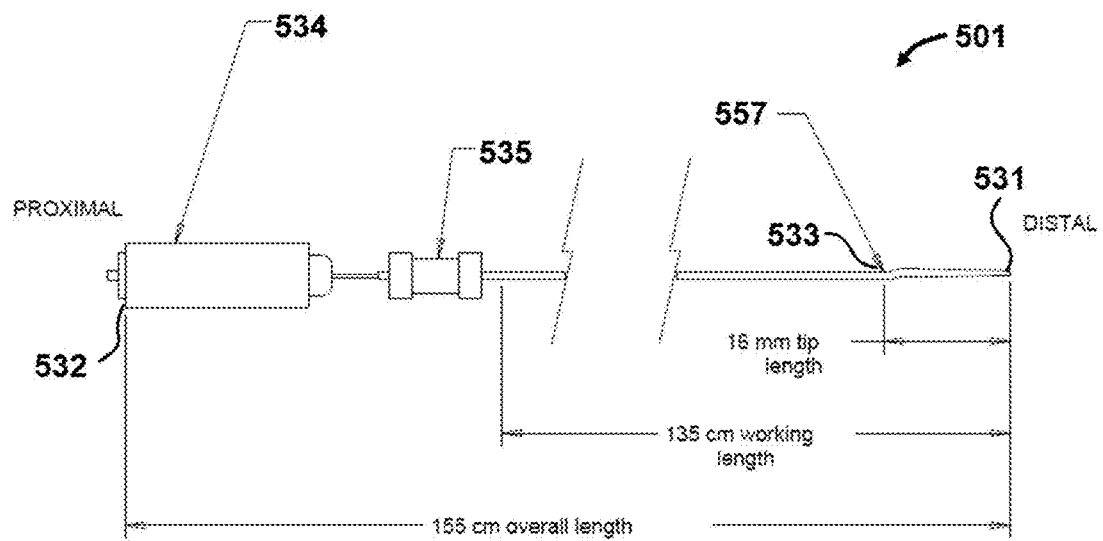
FIG. 7 shows a schematic view of the catheter of FIG. 6.
Figure 8:
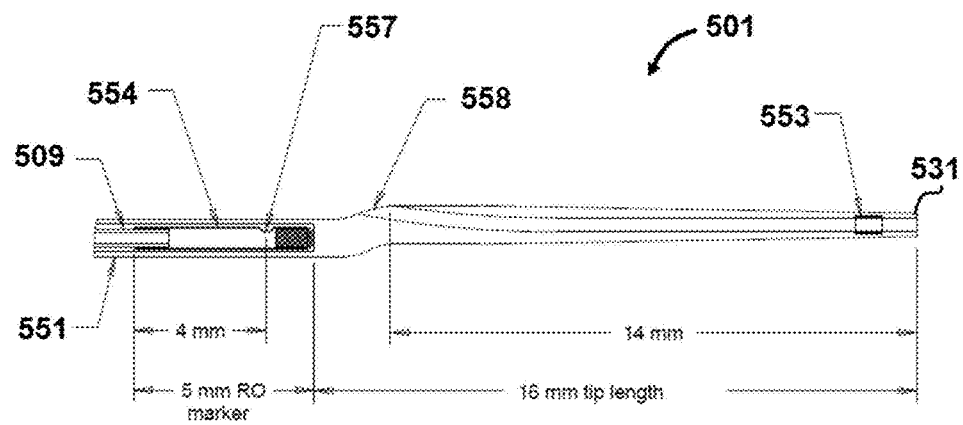
FIG. 8 shows a partial section view of the distal end of catheter of FIG. 7.

A perspective view of patient interface module 502 is shown in FIG. 6, while a schematic view of catheter 501 is shown in FIG. 7, and a partial section view of the distal end of catheter 501 is shown in FIG. 8. As shown in FIG. 7, catheter 501 comprises a bead 535 and an optical connector 534 near proximal end 532. In this embodiment, patient interface module 502 is configured to control catheter 501 via a torque cable 509 (shown in FIG. 8) that transmits torque from patient interface module 502 to distal end 531 of catheter 501, In certain embodiments, patient interface module 502 can be configured to provide 100 mm of linear stroke to catheter 501 at variable translation speeds up to 50 mm per second in two directions (e.g. push forward or pull back). In addition, patient interface module 502 can be configured to rotate an imaging port 533 at speeds up to 3,600 revolutions per minute and obtain 1,000 A-scans per rotation.

In certain embodiments, catheter 501 can be a sterile, single-use disposable catheter with a 3.2 F crossing profile and monorail design compatible with a 6F guide catheter and a 0.014 inch guide wire. In particular embodiments, catheter 501 may comprise a stationary outer sheath 551 with an imaging port 557, a rotating and translating torque cable 509 and optics assembly 552. In specific embodiments, catheter 501 comprises an optical fiber through its length, with an optic assembly (e.g. a ferrule, gradient index [GRIN] lens, and prism) near imaging port 557 and distal end 531 of catheter 501. In addition, catheter 501 may comprise a radiopaque marker 553 on the outer assembly near distal end 531, as well as a radiopaque marker 554 on the inner assembly near imaging port 557. Catheter 501 may further comprise a guidewire exit port 558 near distal end 531. It is understood that the dimensions shown in FIGS. 7 and 8 are merely exemplary, and that other embodiments may comprise configurations with dimensions different from those shown in this embodiment.

Figure 9:
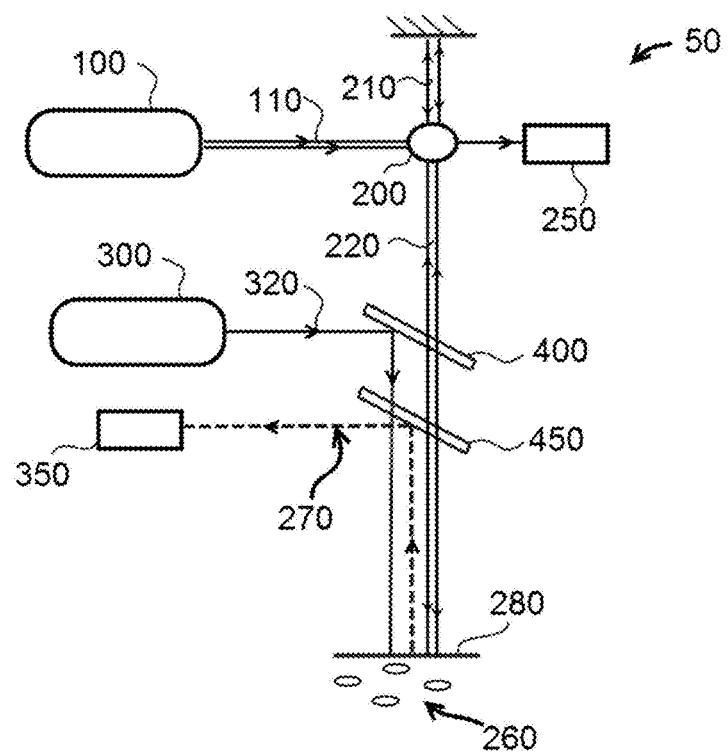
FIG. 9 shows an optical coherence tomography and short-pulsed laser system according to exemplary embodiments.

As previously mentioned, certain embodiments may incorporate optical coherence tomography systems and methods as disclosed in U.S. Patent Publications 2014/0268168 and 2016/0078309 (incorporated by reference herein) to acquire images for analysis. Referring now to FIG. 9, one exemplary embodiment of such an apparatus 50 comprises an optical coherence tomography light source 100, a splitter 200, a short pulsed (e.g. two-photon luminescence) excitation light source 300, a first dichroic element 400 and a second dichroic element 450. It is understood that other embodiments may comprise an apparatus with a different combination of components or fewer components than those shown in FIG. 9.

In this embodiment, optical coherence tomography light source 100 is configured to emit a first wavelength 110 and splitter 200 is configured to direct first wavelength 110 to a reference path 210 and a sample path 220. In certain embodiments, optical coherence tomography light source 100 can be configured as a swept source optical coherence tomography light source or a broadband optical coherence tomography light source. In particular embodiments, sample path 220 can be directed through a photonic crystal fiber. In the embodiment shown, two-photon luminescence excitation light source 300 is configured to emit a second wavelength 320.

During operation, apparatus 50 can be positioned such that sample path 220 and second wavelength 320 are directed to a sample site 280 (e.g. via first dichroic element 400 as well as other components in FIG. 9).

In certain exemplary embodiments, sample site 280 may comprise nanoparticles 260 and in specific embodiments, nanoparticles 260 may be configured as nanorods. In particular embodiments, nanoparticles 260 may be configured as nanorods comprising gold with a surface plasmon resonance of approximately 756 nm. In certain embodiments, the configuration of the nanorods can be selected according to the procedures established in the Example Section 4 provided below.

Apparatus 50 further comprises a photon counting detector 350 configured to detect two-photon luminescence (TPL) and a balanced detector 250 configured to minimize a non-interfering OCT component. In specific embodiments, photon counting detector 350 can be configured as one or more photomultiplier tubes (PMTs). In other embodiments, photon counting detector 350 can be configured as an avalanche photo diode.

In particular embodiments, components of the system illustrated in FIG. 9 can be incorporated into a catheter-based system that utilizes a photonic crystal fiber (PCF) to enable the propagation of light in sample path 220 and second wavelength 320 from TPL excitation light source 300 to sample site 280. The PCF allows single-mode transmission of both OCT and TPL excitation light. Single-mode transmission is required in OCT imaging to insure the modal interference does not occur. Single mode transmission is required for TPL imaging to ensure the pulse duration of TPL excitation light is not broadened due to modal dispersion. In specific embodiments the catheter can be inserted into a blood vessel to obtain intravascular images utilizing system 50.

During operation, system 50 provides the benefits of both OCT and TPL imaging technologies in a single system. In exemplary embodiments, the components of system 50 function according to established principles in OCT and TPL fields. Accordingly, while an overview of the individual OCT and TPL will be provided, it is understood that exemplary embodiments may utilize various combinations of parameters according to environmental conditions or other factors. For example, OCT light source 100 can produce near-infrared light, and the use of relatively long wavelength light allows deeper penetration into the scattering medium such as an arterial wall. In a particular embodiment OCT light source 100 can be configured to provide light at a wavelength of approximately 1310 nm.

As light in sample path 220 is directed at sample site 280, a small portion of this light that reflects from sub-surface features of sample site 280 is collected. During operation, a significant portion of light in sample path 220 is not reflected but, rather, backscatters from the sample. Although backscattered light contributes background that obscures an image in conventional imaging, this light can be used beneficially in OCT systems via interferometry. For example, balanced detector 250 can be used to record the optical path length of received photons, allowing rejection of most photons that multiply scatter in the tissue before detection. This can allow recording three-dimensional images of thick samples to be constructed by rejecting background signal while collecting light directly reflected from regions of interest in sample site 280. In exemplary embodiments, OCT imaging is generally limited to one to two millimeters below the surface in biological tissue in sample site 280. At greater depths, the proportion of light that escapes without scattering is typically too small for detection.

During operation of system 50, TPL light source 300 and photon counting detector 350 are also utilized consistent with established principles in two-photon luminescence microscopy. In certain embodiments, TPL light source 300 can be configured as a tunable femtosecond laser producing excitation energy of second wavelength 320 at 760-1040 nm with a maximum pulse energy of 6 nJ-5 µJ, a pulse width of 100 fs-1 ps, and a repetition rate of 500 kHz-80 MHz. In particular embodiments, TPL light source 300 may also be configured to produce a spot size of 10-30 µm with a spot area of approximately 78-706.8 µm$^2$ and a pixel dwell time of 20 µs. In addition, TPL light source 300 may also be configured to produce 10-1600 pulses per pixel, with an average power on sample of 500-2500 mW, an instantaneous power of 0.0625-5 MW and an instantaneous power density of 2E-4-16E-3 MW/µm$^2$.

In the embodiment shown in FIG. 5, first dichroic element 400 can be positioned to direct second wavelength 320 to sample site 280 via a photonic crystal fiber (PCF). In particular embodiments, the PCF can have a large sized mode field diameter (20 µm) (LMA-20) available from NKT Photonics. In certain embodiments, the PCF may be configured as a double-clad fiber, and in specific embodiments, may be a double-clad high NA fiber such as a model number DC-165-16-Passive Fiber available from Crystal Fibre. Exemplary double-clad photonic crystal fibers may comprise a large-mode area, single-mode core embedded in a high-NA multimode fiber structure. Such fibers can allow a single-mode beam to be propagated forward in the fiber and at the same time scattered light or two-photon luminescence may be collected and propagated backwards for detection. The use of a double-clad fiber instead of a single-clad photonic crystal fiber can increase the two-photon luminescence detection efficiency with a high-NA inner cladding (compared to the low-NA core). It is understood that the particular specifications of components are presented for purposes of example only, and that other embodiments may comprise components with different specifications than those described herein.

During operation of system 50, second wavelength 320 can provide excitation energy to nanoparticles 260, which can emit luminescence 270 that is directed to photon counting detector 350 via second dichroic element 450. In exemplary embodiments, the outputs from the photon counting detector 350 and balanced detector 250 can be configured to be combined in a single display that allows a user to visualize the results of both OCT and TPL imaging overlayed.

Figure 10:
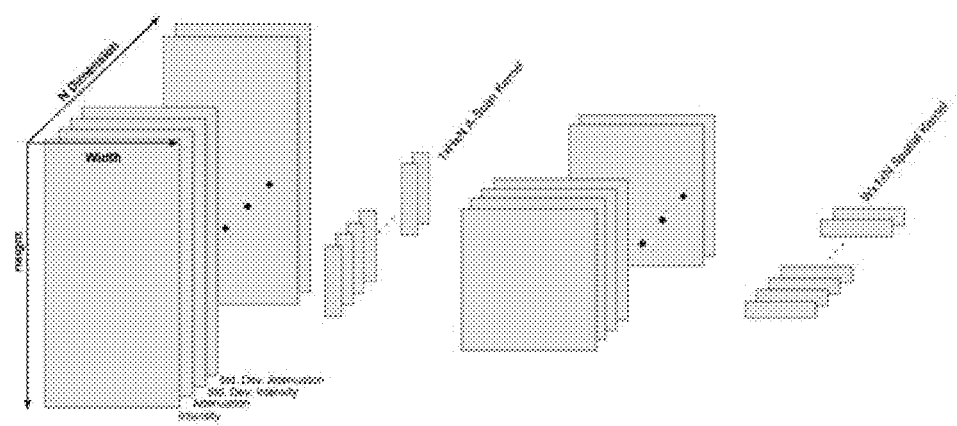
FIG. 10 shows a diagram of a network structure according to an exemplary embodiment.

FIG. 10 illustrates a diagram of a network structure according to an exemplary embodiment utilizing a CNN.

Figure 11:
FIG. 11 shows an in-vivo image produced by an exemplary embodiment.

FIG. 11 illustrates an in-vivo image produced by an exemplary embodiment utilizing a CNN. In the image, calcific plaque is identified in blue (or darker gray, when viewed in grayscale), while fibrous tissue in the artery is shown in green (or lighter gray, when viewed in grayscale).

Figure 12:
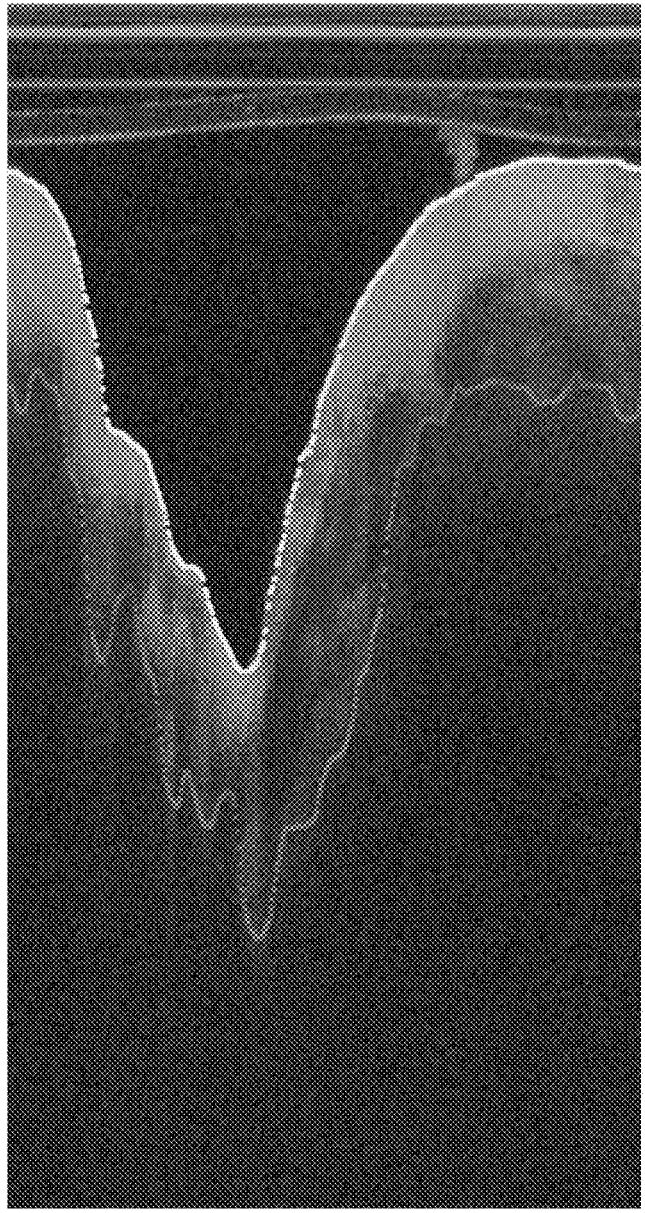
FIG. 12 shows an ex-vivo image produced by an exemplary embodiment.

FIG. 12 illustrates an ex-vivo image produced by an exemplary embodiment utilizing a CNN. In the image, calcific plaque is again identified in blue (or darker gray, when viewed in grayscale), while fibrous tissue in the artery is also shown in green (or lighter gray, when viewed in grayscale).

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:

[1] Yusuf S, Reddy S, Ounpuu S, Anand S, "Global burden of cardiovascular diseases: part I: general considerations, the epidemiologic transition, risk factors, and impact of urbanization," Circulation 104, 2746-2753 (2001)

[2] Libby P, Ridker P M, Maseri A, "Inflammation and Atherosclerosis," Circulation 105, 1135-1143 (2002)

[3] Libby P, Theroux P, "Pathophysiology of coronary artery disease," Circulation 111, 3481-8 (2005)

[4] Lucas A R, Korol R, Pepine C J, "Inflammation in atherosclerosis: some thoughts about acute coronary syndromes," Circulation 113, e728-732 (2006)

[5] Virmani R, Burke A P, Kolodgie F D, Farb A, "Pathology of the Thin-Cap Fibroatheroma: A Type of Vulnerable Plaque," J Intery Cardiol 16(3), 267-272 (2003)

[6] Davies M J, Richardson P D, Woolf N, Katz D R, Mann J, "Risk of thrombosis in human atherosclerotic plaques: role of extracellular lipid, macrophage, and smooth muscle cell content," Br Heart J 69, 377-381 (1993)

[7] Stary H C, Chandler A B, Dinsmore R E, "A definition of advanced types of atherosclerotic lesions and a histological classification of atherosclerosis: a report from the Committee on Vascular Lesions of the Council on Arteriosclerosis," Circulation 92, 1355-1374 (1995)

[8] Jonasson L, Holm J, Skalli O, Bondjers G, Hansson G K, "Regional accumulations of T cells, macrophages, and smooth muscle cells in the human atherosclerotic plaque," Arteriosclerosis 6, 131-138 (1986)

[9] Johnson J L, George S J, Newby A C, Jackson C L, "Divergent effects of matrix metalloproteinases 3, 7, 9, and 12 on atherosclerotic plaque stability in mouse brachiocephalic arteries," Proc Natl Acad Sci 102, 15575-15580 (2005)

[10] Henney A M, Wakeley P R, Davies M J, Foster K, Hembry R, Murphy G, Humphries S, "Localization of stromelysin gene expression in atherosclerotic plaques by in situ hybridization," Proc Natl Acad Sci 88, 8154-8158 (1991)

[11] Galis Z S, Sukhova G K, Lark M W, Libby P, "Increased expression of matrix metalloproteinases and matrix degrading activity in vulnerable regions of human atherosclerotic plaques," J Clin Invest 94, 2493-2503 (1994)

[12] Nikkari S T, O'Brien K D, Ferguson M, Hatsukami T, Welgus H G, Alpers C E, Clowes A W, "Interstitial collagenase (MMP-1) expression in human carotid atherosclerosis," Circulation 92, 1393-1398 (1995)

[13] Libby P, Geng Y J, Aikawa M, Schoenbeck U, Mach F, Clinton S K, Sukhova G K, Lee, R T, "Macrophages and atherosclerotic plaque stability," Curr Opin Lipidol 7, 330-335 (1996)

[14] Taubman M B, Fallon J T, Schecter A D, Giesen P, Mendlowitz M, Fyfe B S, Marmur J D, Nemerson Y, "Tissue factor in the pathogenesis of atherosclerosis," Thromb Haemost 78, 200-204 (1997)

[15] Kolodgie F D, Virmani R, Burke A P, Farb A, Weber D K, Kutys R, Finn A V, Gold H K, "Pathologic assessment of the vulnerable human coronary plaque," Heart 90, 1385-1391 (2004)

[16] van Zandvoort M, Engels W, Douma K, Beckers L, Oude Egbrink M, Daemen M, Slaaf D W, "Two-photon microscopy for imaging of the (atherosclerotic) vascular wall: a proof of concept study," J Vasc Res 41, 54-63 (2004)

[17] Zoumi A, Lu X A, Kassab G S, Tromberg B J, "Imaging coronary artery microstructure using secondharmonic and two-photon fluorescence microscopy," Biophys J 87, 2778-2786 (2004)

[18] Boulesteix T, Pena A M, Pages N, Godeau G, Sauviat M P, Beaurepaire E, Schanne-Klein M C, "Micrometer scale ex vivo multiphoton imaging of unstained arterial wall structure," Cytometry Part A 69A, 20-26 (2006)

[19] Le T T, Langohr I M, Locker M J, Sturek M, Cheng J X, "Label-free molecular imaging of atherosclerotic lesions using multimodal nonlinear optical microscopy," J Biomed Opt 12(5), 0540071-05400710 (2007)

[20] Lilledahl M B, Haugen O A, de Lange Davies C, Svaasand L O, "Characterization of vulnerable plaques by multiphoton microscopy," J Biomed Opt 12(4), 0440051-04400512 (2007)

[21] Wang T, Mancuso J J, Sapozhnikova V, Dwelle J, Ma L L, Willsey B, Kazmi S M, Qiu J, Li X, Asmis R, Johnston K P, Feldman M D, Milner T E, "Dual-wavelength multi-frequency photothermal wave imaging combined with OCT for macrophage and lipid detection in atherosclerotic plaques", J Biomed Opt 17(3), 0360091-03600910 (2012)

[22] Wang T, Mancuso J J, Kazmi S M, Dwelle J, Sapozhnikova V, Willsey B, Ma L L, Qiu J, Li X, Dunn A K, Johnston K P, Feldman M D, Milner T E, "Combined two-photon luminescence microscopy and OCT for macrophage detection in the hypercholesterolemic rabbit aorta using plasmonic gold nanorose", Lasers Surg Med 44(1), 49-59 (2012)

[23] Xue P, Fujimoto J G, "Ultrahigh resolution optical coherence tomography with femtosecond Ti:sapphire laser and photonic crystal fiber," Chinese Science Bulletin 53(13), 1963-1966 (2008)

[24] Ryu S Y, Choi H Y, Na J H, Choi E S, Yang G H, Lee B H, "Optical coherence comography implemented by photonic crystal fiber," Opt Quant Electron 37(13-15), 1191-1198 (2005)

[25] Fu L, Gu M, "Double-clad photonic crystal fiber coupler for compact nonlinear optical microscopy imaging," Opt Lett 31, 1471-1473 (2006)

[26] Liu G, Kieu K, Wise F W, Chen Z, "Multiphoton microscopy system with a compact fiber-based femtosecond-pulse laser and handheld probe," J Biophoton 4, 34-39 (2011).

[27] Fu L, Jain A, Xie H, Cranfield C, Gu M, "Nonlinear optical endoscopy based on a double-clad photonic crystal fiber and a MEMS mirror," Opt Exp 14, 1027-1032 (2006)

[28] Wu Y, Xi J, Cobb M J, Li X, "Scanning fiber-optic nonlinear endomicroscopy with miniature aspherical compound lens and multimode fiber collector," Opt Lett 34, 953-955 (2009)

[29] Kim, E H, Dave, D P, Milner, T E. "Fiber-optic spectral polarimeter using a broadband swept laser source," Optics Communications, 249 351-356 (2005)

[30] Park J, Estrada A, Sharp K, Sang K, Schwartz J A, Smith D K, Coleman C, Payne J D, Korgel B A, Dunn A K, Tunnell J W, "Two-photon-induced photoluminescence imaging of tumors using near-infrared excited gold nanoshells," Opt Exp 16(3), 1590-1599 (2008)

[31] Available at http://sales.hamamatsu.com/assets/pdf/parts_H/m-h7422e.pdf

[32] V. L. Roger, A. S. Go, D. M. Lloyd-Jone, R. J. Adams, J. D. Berry, T. M. Brown, M. R. Carnethon, S. Dai, G. de Simone, E. S. Ford, C. S Fox, H. J. Fullerton, C. Gillespie, K. J. Greenlund, S. M. Hailpern, J. A. Heit, P. M. Ho, V. J. Howard, B. M. Kissela, S. J. Kittner, D. T. Lackland, J. H. Lichtman, L. D. Lisabeth, D. M. Makuc, G. M. Marcus, A. Marelli, D. B. Matchar, M. M. McDermott, J. B. Meigs, C. S. Moy, D. Mozaffarian, M. E. Mussolino, G. Nichol, N. P. Paynter, W. D. Rosamond, P. D. Sorlie, R. S. Stafford, T. N. Turan, M. B. Turner, N. D. Wong and J. Wylie-Rosett, "Heart disease and stroke statistics—2011 update: a report from the American Heart Association," Circulation 123(4), e18-e209 (2011).

[33] E. Falk, P. K. Shah and V. Fuster, "Coronary plaque disruption," Circulation 92(3), 657-671 (1995).

[34] F. D. Kolodgie, R. Virmani, A. P. Burke, A. Farb, D. K. Weber, R. Kutys, A. V. Finn and H. K. Gold, "Pathologic assessment of the vulnerable human coronary plaque," Heart 90(12), 1385-1391 (2004).

[35] N. B. Hao, M. H. Lu, Y. H. Fan, Y. L Cao, Z. R. Zhang, and S. M. Yang, "Macrophages in tumor microenvironments and the progression of tumors," Clin. Dev. Immunol. 2012, 948098-948108 (2012).

[36] B. Ruffell, N. I. Affara, and L. M. Coussens. "Differential macrophage programming in the tumor microenvironment," Trends Immunol. 33(3), 119-126 (2012).

[37] R. Shukla, V. Bansal, M. Chaudhary, A. Basu, R. R. Bhonde, and M. Sastry, "Biocompatibility of gold nanoparticles and their endocytotic fate inside the cellular compartment: a microscopic overview," Langmuir 21(23), 10644-10654 (2005).

[38] M. M. Janat-Amsbury, A. Ray, C. M. Peterson, and H. Ghandehari, "Geometry and surface characteristics of gold nanoparticles influence their biodistribution and uptake by macrophages," Eur. J. Pharm. Biopharm. 77(3), 417-423 (2011).

[39] S. Lal, S. E. Clare, and N. J. Halas, "Nanoshell-enabled photothermal cancer therapy: impending clinical impact," Acc. Chem. Res. 41(12), 1842-1851 (2008).

[40] X. Ji, R. Shao, A. M. Elliott, R. J. Stafford, E. Esparza-Coss, G. Liang, X. P. Luo, K. Park, J. T. Markert, and C. Li, "Bifunctional Gold Nanoshells with a Superparamagnetic Iron Oxide-Silica Core Suitable for Both M R Imaging and Photothermal Therapy," J. Phys. Chem. C 111(17), 6245-6251 (2007).

[41] S. E. Skrabalak, L. Au, X. Lu, X. Li, and Y. Xia, "Gold nanocages for cancer detection and treatment," Nanomedicine (Lond) 2(5), 657-668 (2007).

[42] M. Longmire, P. L. Choyke, and H. Kobayashi, "Clearance properties of nano-sized particles and molecules as imaging agents: considerations and caveats," Nanomedicine (Lond) 3(5), 703-717 (2008).

[43] L. L. Ma, M. D. Feldman, J. M. Tam, A. S. Paranjape, K. K. Cheruku, T. A. Larson, J. O. Tam, D. R. Ingram, V. Paramita, J. W. Villard, J. T. Jenkins, T. Wang, G. D. Clarke, R. Asmis, K. Sokolov, B. Chandrasekar, T. E. Milner, and K. P. Johnston, "Small multifunctional nanoclusters (nanoroses) for targeted cellular imaging and therapy," ACS Nano 3(9), 2686-2696 (2009).

[44] T. Wang, J. J. Mancuso, S. M. Kazmi, J. Dwelle, V. Sapozhnikova, B. Willsey, L. L. Ma, J. Qiu, X. Li, A. K. Dunn, K. P. Johnston, M. D. Feldman, and T. E. Milner, "Combined two-photon luminescence microscopy and OCT for macrophage detection in the hypercholesterolemic rabbit aorta using plasmonic gold nanorose," Lasers Surg. Med. 44(1), 49-59 (2012).

[45] T. S. Hauck, A. A. Ghazani, and W. C. W. Chan, "Assessing the effect of surface chemistry on gold nanorod uptake, toxicity, and gene expression in mammalian cells," Small 4(1), 153-159 (2008).

[46] T. Niidome, M. Yamagata, Y. Okamoto, Y. Akiyama, H. Takahashi, T. Kawano, Y. Katayama, and Y. Niidome, "PEG-modified gold nanorods with a stealth character for in vivo applications," J. Control Release 114(3), 343-347 (2006).

[47] A. Mooradian, "Photoluminescence of metals," Phys. Rev. Lett. 22(5), 185-187 (1969).

[48] J. Zheng, C. Zhang, and R. M. Dickson, "Highly fluorescent, water-soluble, size-tunable gold quantum dots," Phys. Rev. Lett. 93(7), 077402-077405 (2004).

[49] G. Wang, T. Huang, R. W. Murray, L. Menard, and R. G. Nuzzo, "Near-IR luminescence of monolayer-protected metal clusters," J. Am. Chem. Soc. 127(3), 812-813 (2005).

[50] J. P. Wilcoxon, J. E. Martin, F. Parsapour, B. Wiedenman, and D. F. Kelley, "Photoluminescence from nano-size gold clusters," J. Chem. Phys. 108(21), 9137-9143 (1998).

[51] Y. Fang, W. Chang, B. Willingham, P. Swanglap, S. Dominguez-Medina, and S. Link, "Plasmon emission quantum yield of single gold nanorods as a function of aspect ratio," ACS Nano 6(8), 7177-7184 (2012).

[52] P. K. Jain, X. Huang, I. H. El-Sayed, and M. A. El-Sayed, "Review of some interesting surface plasmon resonance-enhanced properties of noble metal nanoparticles and their applications to biosystems," Plasmonics 2(3), 107-118 (2007).

[53] M. A. El-Sayed, "Some interesting properties of metals confined in time and nanometer space of different shapes," Acc. Chem. Res. 34(4), 257-264 (2001).

[54] C. Sönnichsen, T. Franzl, T. Wilk, G. von Plessen, J. Feldmann, O. Wilson, and P. Mulvaney, "Drastic reduction of plasmon damping in gold nanorods," Phys. Rev. Lett. 88, 077402-077405 (2002).

[55] M. B. Mohamed, V. Volkov, S. Link, and M. A. El-Sayed, "The 'lightning' gold nanorods: fluorescence enhancement of over a million compared to the gold metal," Chem. Phys. Lett. 317(6), 517-523 (2000).

[56] S. Link, M. B. Mohamed, and M. A. El-Sayed, "Simulation of the optical absorption spectra of gold nanorods as a function of their aspect ratio and the effect of the medium dielectric constant," J. Phys. Chem. B 106(16), 3073-3077 (1999).

[57] S. S. Verma and J. S. Sekhon, "Influence of aspect ratio and surrounding medium on localized surface plasmon resonance (LSPR) of gold nanorod," J. Optics 41(2), 89-93 (2012).

[58] P. K. Jain, X. Huang, I. H. El-Sayed and M. A. El-Sayed, "Noble metals on the nanoscale: optical and photothermal properties and some applications in imaging, sensing, biology, and medicine," Acc. Chem. Res. 41(12), 1578-1586 (2008).

[59] E. T. Castellana, R. C. Gómez, M. E. Gomez, and D. H. Russell, "Longitudinal surface plasmon resonance based gold nanorod biosensors for mass spectrometry," Langmuir 26(8), 6066-6070 (2010).

[60] H. Wang, T. B. Huff, D. A. Zweifel, W. He, P. S. Low, A. Wei, and J. X. Cheng, "In vitro and in vivo two-photon luminescence imaging of single gold nanorods," Proc. Natl. Acad. Sci. USA 102(44), 15752-15756 (2005).

[61] L. Tong, Q. Wei, A. Wei, and J. X. Cheng, "Gold nanorods as contrast agents for biological imaging: optical properties, surface conjugation and photothermal effects," Photochem. Photobiol. 85(1), 21-32 (2009).

[62] T. Y. Ohulchanskyy, I. Roy, K. T. Yong, H. E. Pudavar, and R. N. Prasad, "High-resolution light microscopy using luminescent nanoparticles," WIREs Nanomed. Nanobiotechnol. 2(2), 162-175 (2010).

[63] D. Nagesha, G. S. Laevsky, P. Lampton, R. Banyal, C. Warner, C. DiMarzio, and S. Sridhar, "In vitro imaging of embryonic stem cells using multiphoton luminescence of gold nanoparticles," Int. J. Nanomedicine 2(4), 813-819 (2007).

[64] Y. Zhang, J. Yu, D. J. S. Birch, and Y. Chen, "Gold nanorods for fluorescence lifetime imaging in biology," J. Biomed. Opt. 15(2), 0205041-0205043 (2010).

[65] C. L. Chen, L. R. Kuo, C. L. Chang, Y. K. Hwu, C. K. Huang, S. Y. Lee, K. Chen, S. J. Lin, J. D. Huang, and Y. Y. Chen, "In situ real-time investigation of cancer cell photothermolysis mediated by excited gold nanorod surface plasmons," Biomaterials 31(14), 4104-4112 (2010).

[66] H. Okamoto and K. Imura, "Near-field imaging of optical field and plasmon wavefunctions in metal nanoparticles," J. Mater. Chem. 16(40), 3920-3928 (2006).

[67] K. Imura, T. Nagahara, and H. Okamoto, "Near-field two-photon-induced photoluminescence from single gold nanorods and imaging of plasmon modes," J. Phys. Chem. B 109(27), 13214-13220 (2005).

[68] W. H. Ni, X. S. Kou, Z. Yang, and J. F. Wang, "Tailoring longitudinal surface plasmon wavelengths, scattering and absorption cross sections of gold nanorods," ACS Nano 2(4), 677-686 (2008).

[69] C. Xu and W. W. Webb, "Measurement of two-photon excitation cross sections of molecular fluorophores with data from 690 to 1050 nm," JOSA B 13(3), 481-491 (1996).

[70] R. Gans, "Form of ultramicroscopic particles of silver," Ann. Phys. 47(10), 270-284 (1915).

[71] M. A. Albota, C. Xu, and W. W. Webb, "Two-photon fluorescence excitation cross sections of biomolecular probes from 690 to 960 nm," Appl. Opt. 37(31), 7352-7356 (1998).

[72] G. T. Boyd, Z. H. Yu, and Y. R. Shen, "Photoinduced luminescence from the noble metals and its enhancement on roughened surfaces," Phys. Rev. B 33(12), 7923-7936 (1986).

[73] S. Eustis and M. A. El-Sayed, "Aspect ratio dependence of the enhanced fluorescence intensity of gold nanorods: experimental and simulation study," J. Phys. Chem. B 109(34), 16350-16356 (2005).

[74] M. Guerrisi and R. Rosei, "Splitting of the interband absorption edge in Au", Phys. Rev. B 12(2), 557-563 (1975).

[75] X. Huang, S. Neretina, and M. A. El-Sayed, "Gold nanorods: from synthesis and properties to biological and biomedical applications," Adv. Mater. 21(48), 4880-4910 (2009).

[76] K. S. Lee and M. A. El-Sayed, "Dependence of the enhanced optical scattering efficiency relative to that of absorption for gold metal nanorods on aspect ratio, size, end-cap shape and medium refractive index," J. Phys. Chem. B 109(43), 20331-20338 (2005).

[77] C. Sönnichsen and A. P. Alivisatos, "Gold nanorods as novel nonbleaching plasmon-based orientation sensors for polarized single-particle microscopy," Nano Lett. 5(2), 301-304 (2005).

[78] S. Link, C. Burda, B. Nikoobakht, and M. A. El-Sayed, "Laser-induced shape changes of colloidal gold nanorods using femtosecond and nanosecond laser pulses" J. Phys. Chem. B 104(26), 6152-6163 (2000).

[79] A. Bouhelier, R. Bachelot, G. Lerondel, S. Kostcheev, P. Royer, G. P. Wiederrecht, "Surface plasmon characteristics of tunable photoluminescence in single gold nanorods," Phys. Rev. Lett. 95(26), 2674051-2674054 (2005).

[80] R. E. Hummel, Electronic Properties of Materials, 37-61, 4th ed. (Springer, New York, 2011).

[81] R. Rosei, and P. Winsemius, "Splitting of the interband absorption edge in Au," Phys. Rev. B 12(2), 557-563 (1975).

[82] Tearney G J, Regar E, Akasaka T et al. Consensus standards for acquisition, measurement, and reporting of intravascular optical coherence tomography studies: a report from the International Working Group for Intravascular Optical Coherence Tomography Standardization and Validation. J Am Coll Cardiol 2012; 59:1058-72.

[83] Tearney G J, Yabushita H, Houser S L et al. Quantification of macrophage content in atherosclerotic plaques by optical coherence tomography. Circulation 2003; 107:113-9.

[84] MacNeill B D, Jang I K, Bouma B E et al. Focal and multi-focal plaque macrophage distributions in patients with acute and stable presentations of coronary artery disease. J Am Coll Cardiol 2004; 44:972-9.

[85] Tahara S, Morooka T, Wang Z et al. Intravascular optical coherence tomography detection of atherosclerosis and inflammation in murine aorta. Arterioscler Thromb Vasc Biol 2012; 32:1150-7.

[86] Raffel O C, Tearney G J, Gauthier D D, Halpern E F, Bouma B E, Jang I K. Relationship between a systemic inflammatory marker, plaque inflammation, and plaque characteristics determined by intravascular optical coherence tomography. Arterioscler Thromb Vasc Biol 2007; 27:1820-7.

[87] Raffel O C, Merchant F M, Tearney G J et al. In vivo association between positive coronary artery remodelling and coronary plaque characteristics assessed by intravascular optical coherence tomography. Eur Heart J 2008; 29:1721-8.

[88] Chia S, Raffel O C, Takano M, Tearney G J, Bouma B E, Jang I K. Comparison of coronary plaque characteristics between diabetic and non-diabetic subjects: An in vivo optical coherence tomography study. Diabetes Res Clin Pract 2008; 81:155-60.

[89] Tanaka A, Tearney G J, Bouma B E. Challenges on the frontier of intracoronary imaging: atherosclerotic plaque macrophage measurement by optical coherence tomography. J Biomed Opt 2010; 15:011104.

[90] Ali Z A, Roleder T, Narula J et al. Increased thin-cap neoatheroma and periprocedural myocardial infarction in drug-eluting stent restenosis: multimodality intravascular imaging of drug-eluting and bare-metal stents. Circ Cardiovascular Interv 2013; 6:507-17.

[91] Cilingiroglu M, Oh J H, Sugunan B et al. Detection of vulnerable plaque in a murine model of atherosclerosis with optical coherence tomography. Catheter Cardiovasc Interv 2006; 67:915-23.

[92] Virmani R, Kolodgie F D, Burke A P, Farb A, Schwartz S M. Lessons from sudden coronary death—A comprehensive morphological classification scheme for atherosclerotic lesions. Arterioscler Thromb Vasc Biol 2000; 20:1262-1275.
[93] Bornstein P, Sage H. Structurally distinct collagen types. Annu Rev Biochem 1980; 49:957-1003.
[94] Falk E, Nakano M, Bentzon J F, Finn A V, Virmani R. Update on acute coronary syndromes: the pathologists' view. Eur Heart J 2013; 34:719-28.
[95] Tavakoli S, Zamora D, Ullevig S, Asmis R. Bioenergetic profiles diverge during macrophage polarization: implications for the interpretation of $^{18}$F-FDG PET imaging of atherosclerosis. J Nucl Med 2013; 54:1661-7.
[96] Mourant J R, Freyer J P, Hielscher A H, Eick A A, Shen D, Johnson T M. Mechanisms of light scattering from biological cells relevant to noninvasive optical-tissue diagnostics. Appl Opt 1998; 37:3586-3593.
[97] van der Meer F J, Faber D J, Baraznji Sassoon D M, Aalders M C, Pasterkamp G, van Leeuwen T G. Localized measurement of optical attenuation coefficients of atherosclerotic plaque constituents by quantitative optical coherence tomography. IEEE Trans Med Imaging 2005; 24:1369-76.
[98] Wang T, Mancuso J J, Kazmi S M et al. Combined two-photon luminescence microscopy and OCT for macrophage detection in the hypercholesterolemic rabbit aorta using plasmonic gold nanorose. Lasers Surg Med 2012; 44:49-59.
[99] Phipps J E, Sun Y, Saroufeem R, Hatami N, Fishbein M C, Marcu L. Fluorescence lifetime imaging for the characterization of the biochemical composition of atherosclerotic plaques. J Biomed Opt 2011; 16:096018.
[100] van Soest G, Regar E, Goderie T P et al. Pitfalls in plaque characterization by OCT: image artifacts in native coronary arteries. J Am Coll Cardiol Img 2011; 4:810-3.
[101] Nadra I, Mason J C, Philippidis P et al. Proinflammatory activation of macrophages by basic calcium phosphate crystals via protein kinase C and MAP kinase pathways: a vicious cycle of inflammation and arterial calcification? Circ Res 2005; 96:1248-56.
[102] Rajamaki K, Lappalainen J, Oorni K et al. Cholesterol crystals activate the NLRP3 inflammasome in human macrophages: a novel link between cholesterol metabolism and inflammation. PLoS One 2010; 5:e11765.
[103] Marcu L, Jo J A, Fang Q et al. Detection of rupture-prone atherosclerotic plaques by time-resolved laser-induced fluorescence spectroscopy. Atherosclerosis 2009; 204:156-64.
[104] Motz J T, Fitzmaurice M, Miller A et al. In vivo Raman spectral pathology of human atherosclerosis and vulnerable plaque. J Biomed Opt 2006; 11:021003.
[105] Maldonado N, Kelly-Arnold A, Vengrenyuk Y et al. A mechanistic analysis of the role of microcalcifications in atherosclerotic plaque stability: potential implications for plaque rupture. Am J Physiol Heart Circ Physiol 2012; 303:H619-28.
[106] Bostrom K, Watson K E, Horn S, Wortham C, Herman I M, Demer L L. Bone morphogenetic protein expression in human atherosclerotic lesions. J Clin Invest 1993; 91:1800-9.
[107] Manfrini O, Mont E, Leone O et al. Sources of error and interpretation of plaque morphology by optical coherence tomography. Am J Cardiol 2006; 98:156-9.
[108] Rieber J, Meissner O, Babaryka G et al. Diagnostic accuracy of optical coherence tomography and intravascular ultrasound for the detection and characterization of atherosclerotic plaque composition in ex-vivo coronary specimens: a comparison with histology. Coron Artery Dis 2006; 17:425-30.
[109] Kume T, Akasaka T, Kawamoto T et al. Assessment of coronary arterial plaque by optical coherence tomography. Am J Cardiol 2006; 97:1172-5.
[110] Virmani R, Kolodgie 1-D, Burke A P, Farb A, Schwartz S M. Lessons from sudden coronary death—A comprehensive morphological classification scheme for atherosclerotic lesions. Arterioscler Thromb Vasc Biol 2000; 20:1262-1275.
[111] Tearney G J, Yabushita H, Houser S L, et al. Quantification of macrophage content in atherosclerotic plaques by optical coherence tomography. Circulation 2003; 107: 113-9.
[112] MacNeill B D, Jang I K, Bouma B E, et al. Focal and multi-focal plaque macrophage distributions in patients with acute and stable presentations of coronary artery disease. J Am Coll Cardiol 2004; 44:972-9.
[113] Athanasiou L S, Bourantas C V, Rigas G et al. Methodology for fully automated segmentation and plaque characterization in intracoronary optical coherence tomography images. J Biomed Opt 2014; 19: 026009.
[114] Chen, T. C. et al. Spectral Domain Optical Coherence Tomography and Glaucoma. International ophthalmology clinics 2008; 48.4: 29-45. PMC. Web.
[115] Christensen, C. M., Jerome G. H., and Hwang, J. The Innovator's Prescription: A Disruptive Solution for Health Care. New York: McGraw-Hill, 2009. Print.
[116] Choma, M. A., et al. Sensitivity advantage of swept source and Fourier domain optical coherence tomography. Optics express 2003; 11.18: 2183-2189.
[117] Fujii K, Hao H, Shibuya M et al. Accuracy of OCT, Grayscale IVUS, and Their Combination for the Diagnosis of Coronary TCFA: An Ex Vivo Validation Study. JACC Cardiovasc Imaging 2015; 8:451-60.
[118] Jang, Ik-Kyung et al. Visualization of Coronary Atherosclerotic Plaques in Patients Using Optical Coherence Tomography: Comparison with Intravascular Ultrasound. Journal of the American College of Cardiology 2002; 39.4: 604-09. Web.
[119] Manfrini O, Mont E, Leone O et al. Sources of error and interpretation of plaque morphology by optical coherence tomography. The American journal of cardiology 2006; 98:156-9.
[120] Standaert, Michael. "Cybersecurity: The Age of the Megabreach." MIT Technology Review 2016; 119.2: 69-77. Web.
[121] Swada, T. et al. Feasibility of combined use of intravascular ultrasound radiofrequency data analysis and optical coherence tomography for detecting thin-cap fibroatheroma. European Heart Journal 2008; 29: 1136-1146. Web.
[122] Tearney, Guillermo J et al. Consensus Standards for Acquisition, Measurement, and Reporting of Intravascular Optical Coherence Tomography Studies. Journal of the American College of Cardiology 2012; 59.12: 1058-072. Web.
[123] Ughi G J, Adriaenssens T, Sinnaeve P, Desmet W, D'Hooge J. Automated tissue characterization of in vivo atherosclerotic plaques by intravascular optical coherence tomography images. Biomed Opt Express 2013; 4:1014-30.
[124] Gessert, N., Lutz, M., Heyder, M., Latus, S., Leistner, D. M., Abdelwahed, Y. S., & Schlaefer, A. (2018). Automatic Plaque Detection in IVOCT Pullbacks Using Convolutional Neural Networks. IEEE transactions on medical imaging.

[125] Gessert, N., Heyder, M., Latus, S., Lutz, M., & Schlaefer, A. (2018). Plaque Classification in Coronary Arteries from IVOCT Images Using Convolutional Neural Networks and Transfer Learning. arXiv preprint arXiv:1804.03904.

[126] Miyagawa, M., Costa, M. G. F., Gutierrez, M. A., Costa, J. P. G. F., & Costa Filho, C. F. F. (2018, July). Lumen Segmentation in Optical Coherence Tomography Images using Convolutional Neural Network. In 2018 40th Annual International Conference of the IEEE Engineering in Medicine and Biology Society (EMBC) (pp. 600-603). IEEE.

The invention claimed is:

1. A method of improving discrimination between superficial lipid and calcium versus fibrous tissue and lipid, calcium tissues, and connective tissue, the method comprising:
   (1) creating a database of a-scans characteristic of each fibrous, calcium, lipid, and connective tissue based on histology and user input;
   (2) parsing individual a-scans one at a time from a b-scans;
   (3) delimiting a tissue region;
   (4) identifying an index of an initiation of a signal decay region;
   (5) identifying an index of a termination of the signal decay region;
   (6) calculating a goodness-of-fit (GOF) to a Gaussian function;
   (7) extracting a denominator coefficient in the Gaussian function;
   (8) calculating an area under a signal decay region;
   (9) calculating an area under a total delimited tissue region; and
   (10) inputting statistics from steps (4) and (5) into a linear discrimination analysis (LDA) trained on the database to classify an a-scan as fibrous, calcium or lipid.

2. The method of claim 1 further comprising biasing thresholds on a neural network based on a-scan classification obtained in step (10) of claim 1.

3. The method of claim 1 wherein delimiting a tissue region comprises sampling from a start of a lumen to a point where an intensity is five percent of a maximum intensity.

4. The method of claim 1 wherein identifying an index of an initiation of a signal decay region comprises:
   using a panning window algorithm where slope is calculated between intensity values at end points of a window; and
   determining a signal decay region when five consecutive windows show a negative slope.

5. The method of claim 1 wherein identifying an index of a termination of the signal decay region comprises identifying five consecutive windows with positive slope in the signal decay region.

* * * * *